(12) United States Patent
Wang et al.

(10) Patent No.: US 8,067,596 B2
(45) Date of Patent: Nov. 29, 2011

(54) PROCESSES FOR THE PRODUCTION OF (+)-"NAL" MORPHINAN COMPOUNDS

(75) Inventors: Peter X. Wang, Clarkson Valley, MO (US); Tao Jiang, St. Louis, MO (US); Gary L. Cantrell, Troy, IL (US); David W. Berberich, St. Peters, MO (US); Bobby N. Trawick, Florissant, MO (US); Subo Liao, Ballwin, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 469 days.

(21) Appl. No.: 12/316,974

(22) Filed: Dec. 17, 2008

(65) Prior Publication Data

US 2009/0156820 A1    Jun. 18, 2009

Related U.S. Application Data

(60) Provisional application No. 61/014,102, filed on Dec. 17, 2007.

(51) Int. Cl.
*C07D 221/18*    (2006.01)
*C07D 221/22*    (2006.01)

(52) U.S. Cl. ............................................. 546/43; 546/45
(58) Field of Classification Search ........................ None
See application file for complete search history.

(56) References Cited

U.S. PATENT DOCUMENTS 4,472,253 A    9/1984    Schwartz

FOREIGN PATENT DOCUMENTS

| EP | 0 039 066 | 4/1981 |
| EP | 0 158 476 | 10/1985 |
| GB | 1119270 | 7/1968 |
| WO | WO 95/31463 | 11/1995 |
| WO | WO 99/02529 | 1/1999 |
| WO | WO 2006/138020 | 12/2006 |

*Primary Examiner* — Yong Chu
*Assistant Examiner* — Michael Barker

(57) ABSTRACT

The invention generally provides processes and intermediate compounds useful for the production of (+) nal morphinan compounds. In particular, the process encompasses synthetic routes for the production of (+) nal morphinan compounds or derivatives of (+) nal morphinan compounds from (+)-morphinan substrates such as (+)-hydrocodone, (+)-norhydrocodone or derivatives of either compound.

10 Claims, No Drawings

PROCESSES FOR THE PRODUCTION OF (+)-"NAL" MORPHINAN COMPOUNDS

CROSS-REFERENCE TO RELATED APPLICATION

This application claims priority from Provisional Application Ser. No. 61/014,102 filed on Dec. 17, 2007, which is hereby incorporated by reference in its entirety.

FIELD OF THE INVENTION

The present invention generally relates to processes and intermediate compounds useful for the production of (+)-opiates. In particular, the invention generally provides processes and intermediate compounds for producing (+)-nal morphinan compounds.

BACKGROUND OF THE INVENTION

"(−)-Nal" morphinan compounds, such as naltrexone, naloxone, nalmefene, and nalbuphine, are used in therapeutic applications as analgesics and antagonists. Recently, the (+)-nal morphinan enantiomers have been shown to have important bioactivities that differ from their (−) counterparts. In order to explore the possible benefits of these compounds, there is a need in the art for processes to prepare (+)-nal morphinan compounds.

SUMMARY OF THE INVENTION

Among the various aspects of the present invention is the provision of processes for the preparation of (+)-nal morphinan compounds. One aspect of the invention provides a process for preparing compound 2-1. The process comprises contacting compound 2-1(a) with a halogen, X, to form compound 2-1(b), and contacting compound 2-1(b) with a proton acceptor to form compound 2-1 according to the reaction scheme:

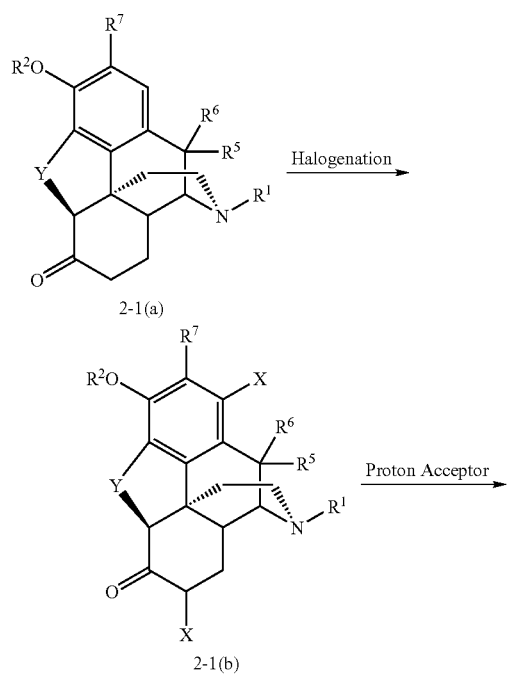

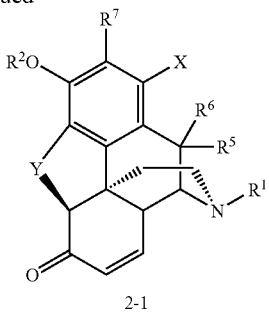

wherein:
R$^1$ and R$^2$ are independently selected from the group consisting of hydrogen, hydrocarbyl, substituted hydrocarbyl, and a protecting group;
R$^5$, and R$^6$ are independently selected from the group consisting of hydrogen, halogen, hydroxyl, NH$_2$, CN, hydrocarbyl, and substituted hydrocarbyl;
R$^7$ is selected from the group consisting of hydrogen and hydroxyl; and
Y is selected from the group consisting of oxygen, sulfur, and nitrogen.

Another aspect of the invention encompasses a process for preparing compound 3. The process comprises contacting compound 2 with (R$^0$CO)$_2$O in the presence of R$^7$CO$_2$M to form compound 3 according to the reaction scheme:

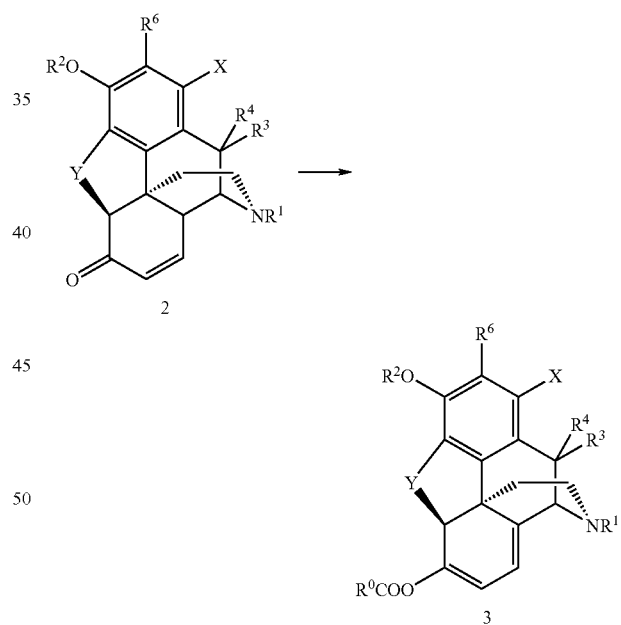

wherein:
R$^0$ is selected from the group consisting of alkyl, substituted alkyl, aryl, and substituted aryl;
R$^1$ and R$^2$ are independently selected from the group consisting of hydrogen, hydrocarbyl, substituted hydrocarbyl, and a protecting group;
R$^3$, and R$^4$ are independently selected from the group consisting of hydrogen, halogen, hydroxyl, NH$_2$, SH, hydrocarbyl, and substituted hydrocarbyl, wherein R$^3$, and R$^4$ may together form a group selected from the group consisting of =O, and =S;

R[6] is selected from the group consisting of hydrogen, halogen, hydroxyl, NH$_2$, CN, hydrocarbyl, and substituted hydrocarbyl;

R[7] is selected from the group consisting of hydrocarbyl or substituted hydrocarbyl;

M is a metal atom selected from the group consisting of Li, Na, and K;

X is selected from the group consisting of halogen and hydrogen; and

Y is selected from the group consisting of oxygen, sulfur, and nitrogen.

A further aspect of the invention encompasses a process for preparing compound 5. The process comprises contacting compound 3 with an oxidizing agent to form compound 4, and then reducing compound 4 to form compound 5 according to the reaction scheme:

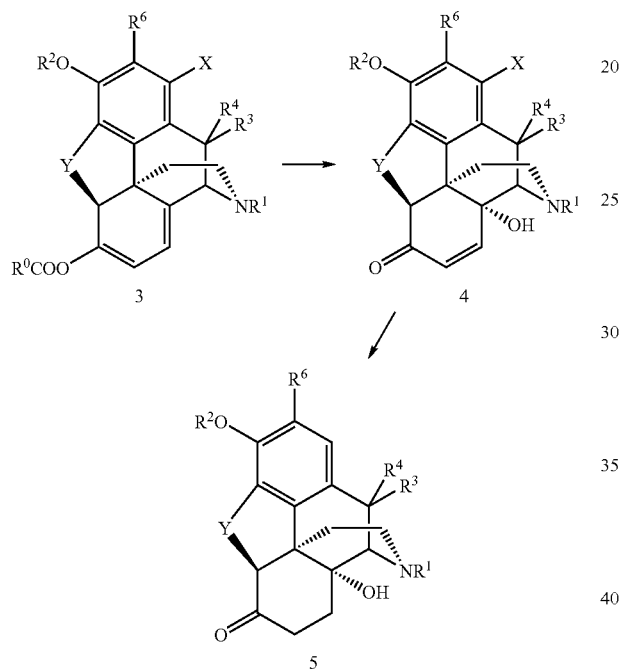

wherein:

R[0] is selected from the group consisting of alkyl, substituted alkyl, aryl, and substituted aryl;

R[1] and R[2] are independently selected from the group consisting of hydrogen, hydrocarbyl, substituted hydrocarbyl, and a protecting group;

R[3], and R[4] are independently selected from the group consisting of hydrogen, halogen, hydroxyl, NH$_2$, SH, hydrocarbyl, and substituted hydrocarbyl, wherein R[3], and R[4] may together form a group selected from the group consisting of =O, and =S;

R[6] is selected from the group consisting of hydrogen, halogen, hydroxyl, NH$_2$, CN, hydrocarbyl, and substituted hydrocarbyl;

X is selected from the group consisting of halogen and hydrogen; and

Y is selected from the group consisting of oxygen, sulfur and nitrogen.

Still another aspect of the invention provides a process for preparing compound 6. The process comprises contacting compound 5a with a N-demethylation agent in the presence of a proton acceptor to form compound 6 according to the reaction scheme:

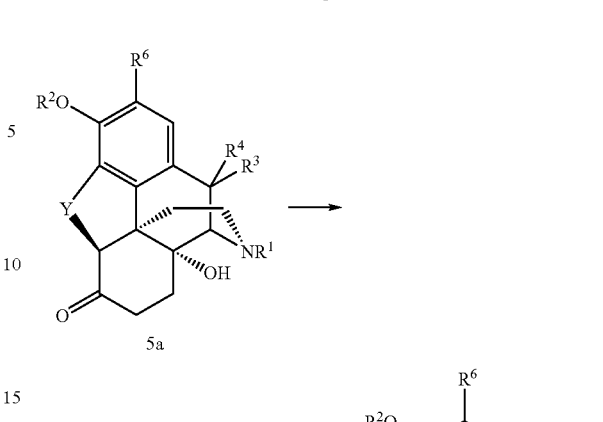

wherein:

R[1a] is {—}OCOR[3a];

R[1] is methyl;

R[2] is selected from the group consisting of hydrogen, hydrocarbyl, substituted hydrocarbyl, and a protecting group;

R[3a] is selected from the group consisting of hydrocarbyl, and substituted hydrocarbyl;

R[3], and R[4] are independently selected from the group consisting of hydrogen, halogen, hydroxyl, NH$_2$, SH, hydrocarbyl, and substituted hydrocarbyl, wherein R[3], and R[4] may together form a group selected from the group consisting of =O, and =S;

R[6] is selected from the group consisting of hydrogen, halogen, hydroxyl, NH$_2$, CN, hydrocarbyl, and substituted hydrocarbyl; and Y is selected from the group consisting of oxygen, sulfur, and nitrogen.

Another aspect of the invention encompasses a process for the preparation of compound 7. The process comprises contacting compound 6a with a proton donor to form compound 7 according to the reaction scheme:

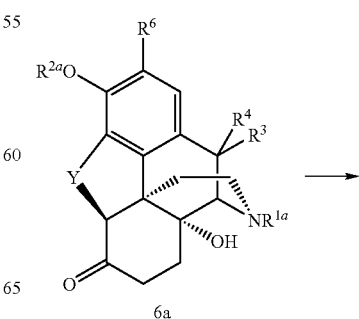

-continued

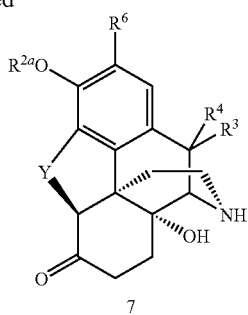

7 wherein:

$R^{1a}$ is {—}OCOR$^{3a}$;

$R^{2a}$ is selected from the group consisting of hydrogen, alkyl, substituted alkyl, aryl, substituted aryl, and acyl;

$R^{3a}$ is hydrocarbyl, and substituted hydrocarbyl;

$R^3$, and $R^4$ are independently selected from the group consisting of hydrogen, halogen, hydroxyl, NH$_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, NH$_2$, CN, hydrocarbyl, and substituted hydrocarbyl; and Y is selected from the group consisting of oxygen, sulfur, and nitrogen.

A further aspect of the invention provides a process for the preparation of compound 7a. The process comprises contacting compound 6a with an agent selected from the group consisting of a proton donor, and an O-demethylating agent; to form compound 7a according to the reaction scheme:

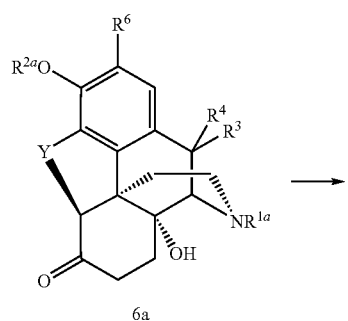

6a

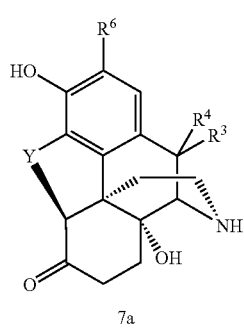

7a wherein:

$R^{1a}$ is {—}OCOR$^{3a}$;

$R^{2a}$ is selected from the group consisting of hydrogen, alkyl, substituted alkyl, aryl, substituted aryl, and acyl;

$R^{3a}$ is hydrocarbyl, and substituted hydrocarbyl;

$R^3$, and $R^4$ are independently selected from the group consisting of hydrogen, halogen, hydroxyl, NH$_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, NH$_2$, CN, hydrocarbyl, and Y is selected from the group consisting of oxygen, sulfur, and nitrogen.

Yet another aspect of the invention encompasses a process for preparing compound 8. The process comprises contacting compound 7 with R$^1$X to form compound 8 according to the reaction scheme:

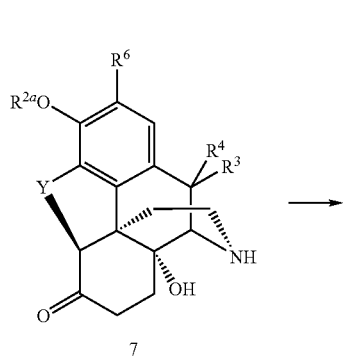

7

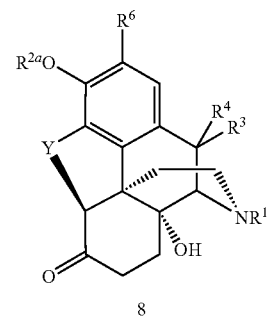

8 wherein:

$R^1$ is selected from the group consisting of hydrocarbyl, and substituted hydrocarbyl;

$R^{2a}$ is selected from the group consisting of hydrogen, alkyl, substituted alkyl, aryl, substituted aryl, and acyl;

$R^3$, and $R^4$ are independently selected from the group consisting of hydrogen, halogen, hydroxyl, NH$_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, NH$_2$, CN, hydrocarbyl, and substituted hydrocarbyl;

X is a halogen; and

Y is selected from the group consisting of oxygen, sulfur, and nitrogen.

Another aspect of the invention provides a process for the preparation of compound 8-1 according to the following reaction scheme:

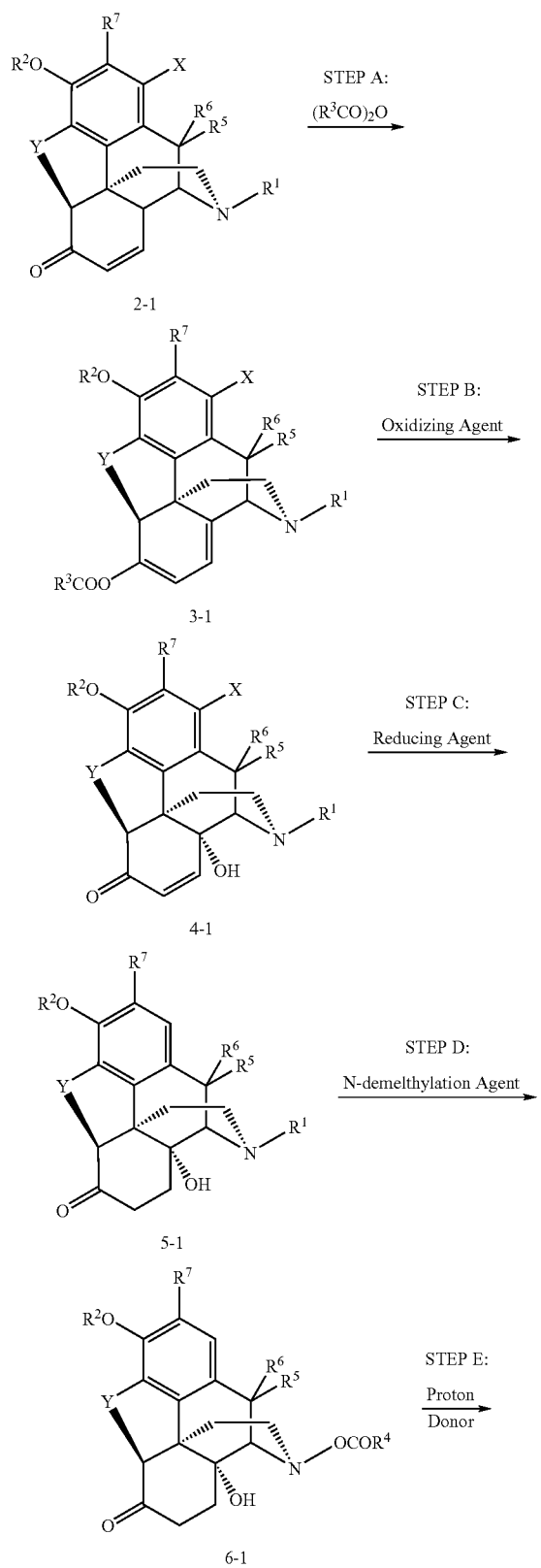

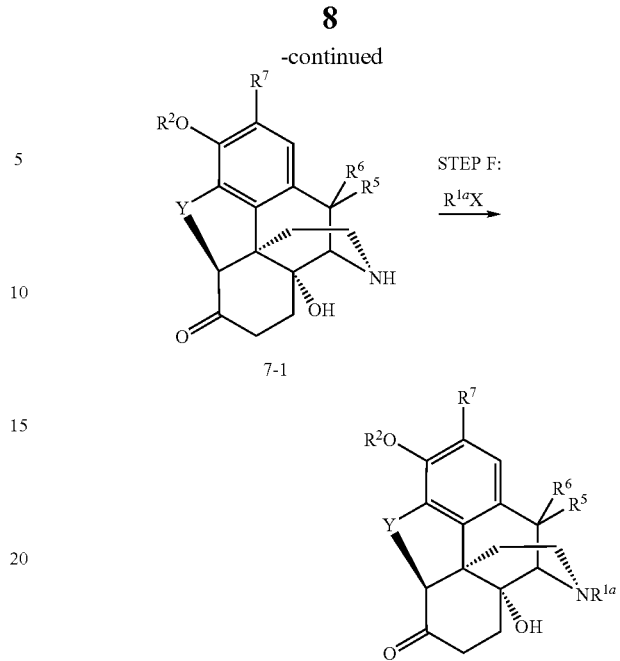

wherein:
R¹ and R² are independently selected from the group consisting of hydrogen and methyl;
R¹ᵃ is selected from the group consisting of hydrocarbyl, and substituted hydrocarbyl;
R³ is alkyl, substituted alkyl, aryl, and substituted aryl;
R⁴ is hydrocarbyl, and substituted hydrocarbyl;
R⁵, and R⁶ are independently selected from the group consisting of hydrogen, halogen, hydroxyl, $NH_2$, SH, hydrocarbyl, and substituted hydrocarbyl, wherein R⁵, and R⁶ may together form a group selected from the group consisting of =O, and =S;
R⁷ is selected from the group consisting of hydrogen, halogen, hydroxyl, $NH_2$, CN, hydrocarbyl, and substituted hydrocarbyl;
X is selected from the group consisting of halogen and hydrogen; and
Y is selected from the group consisting of oxygen, sulfur, and nitrogen.

Other aspects and features of the invention are detailed below.

DETAILED DESCRIPTION OF THE INVENTION

The present invention provides processes and intermediate compounds for producing (+) nal morphinan compounds. In particular, the process encompasses synthetic routes for the production of (+) nal morphinan compounds or derivatives of (+) nal morphinan compounds from (+)-morphinan substrates such as (+)-hydrocodone, (+)-norhydrocodone or derivatives of either compound. While it is envisioned that the synthetic routes described herein may be utilized to produce (+/−)-nal morphinan compounds, in an exemplary aspect of the invention, the process encompasses the production of (+)-nal morphinan compounds or derivatives of (+)-nal morphinan compounds.

(I) Process for Preparation of (+)-Nal Morphinans

One aspect of the invention provides processes for the preparation of (+)-nal morphinans. For purposes of illustration, Reaction Scheme 1 depicts the production of compound 8-1 (i.e., (+)-nal morphinans) from compound 2-1 (i.e., (+)-opioid derivative) in accordance with one aspect of the present invention:

Reaction Scheme 1

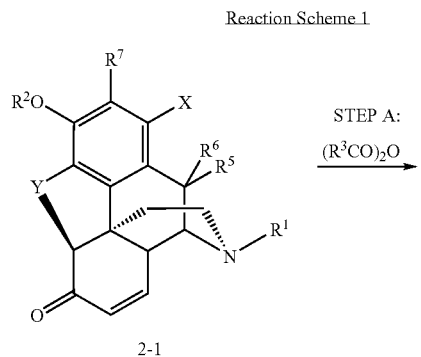

2-1

STEP A:
$(R^3CO)_2O$

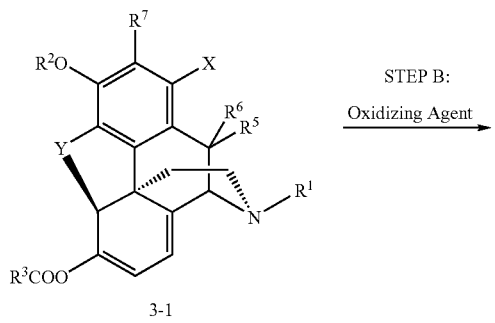

3-1

STEP B:
Oxidizing Agent

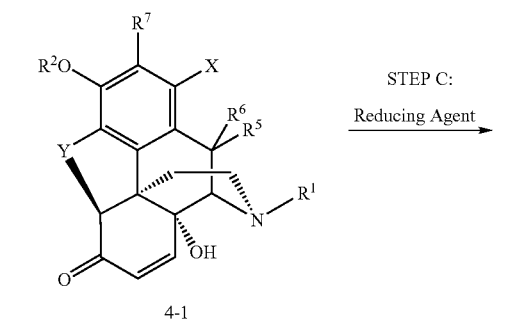

4-1

STEP C:
Reducing Agent

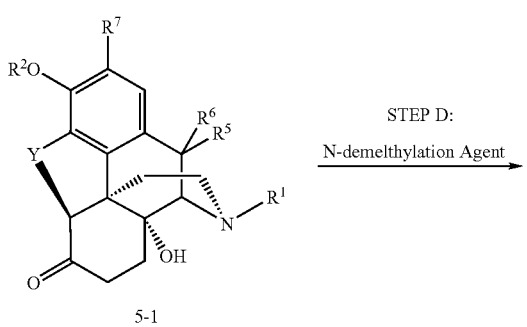

5-1

STEP D:
N-demelthylation Agent

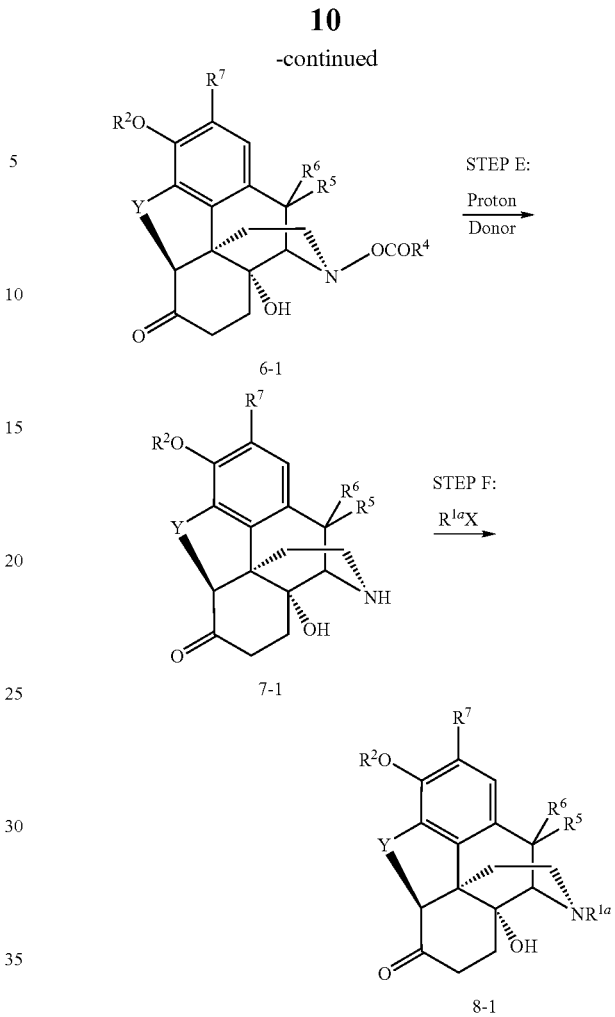

wherein:
- $R^1$ and $R^2$ are independently selected from the group consisting of hydrogen and methyl;
- $R^{1a}$ is selected from the group consisting of hydrocarbyl, and substituted hydrocarbyl;
- $R^3$ is selected from the group consisting of alkyl, substituted alkyl, aryl, and substituted aryl;
- $R^4$ is selected from the group consisting of hydrocarbyl, and substituted hydrocarbyl;
- $R^5$, and $R^6$ are independently selected from the group consisting of hydrogen, halogen, hydroxyl, $NH_2$, SH, hydrocarbyl, and substituted hydrocarbyl, wherein $R^5$, and $R^6$ may together form a group selected from the group consisting of =O, and =S;
- $R^7$ is selected from the group consisting of hydrogen, halogen, hydroxyl, $NH_2$, CN, hydrocarbyl, and substituted hydrocarbyl;
- X is selected from the group consisting of halogen and hydrogen; and
- Y is selected from the group consisting of oxygen, sulfur, and nitrogen.

In an exemplary embodiment, $R^{1a}$ is selected from the group consisting of alkyl, vinyl, aryl, {—}$CH_2$-aryl; $R^2$ is hydrogen; $R^4$ is selected from the group consisting of alkyl, vinyl, aryl, {—}$CH_2$-aryl; $R^5$, $R^6$, and $R^1$ are each hydrogen, X is bromide; and Y is oxygen. Included among some of the more preferred hydrocarbyl groups for $R^{1a}$, are methyl, ethyl, propyl, isopropyl, butyl, isobutyl, tertiary butyl, pentyl, {—}CH$_2$-vinyl, {—}CH$_2$-cyclopropyl, {—}CH$_2$ cyclobutyl, {—}CH$_2$-cyclopentyl, {—}CH$_2$-cyclohexyl, {—}CH$_2$-phenyl, {—}CH$_2$-methylphenyl, or {—}CH$_2$-benzyl.

(a) Preparation of Compound 2-1

Compound 2-1 may be prepared via a variety of synthetic routes without deviating from the scope of the invention. In one iteration of the invention, compound 2-1 may be prepared from compound 1-1. In another iteration, compound 2-1 may be prepared from compound 2-1(b). Both processes are described in detail below.

(i) Preparation from Compound 1-1

In one embodiment, the substrate for preparation of compound 2-1 corresponds to compound 1-1 depicted in accordance with the following Reaction Scheme:

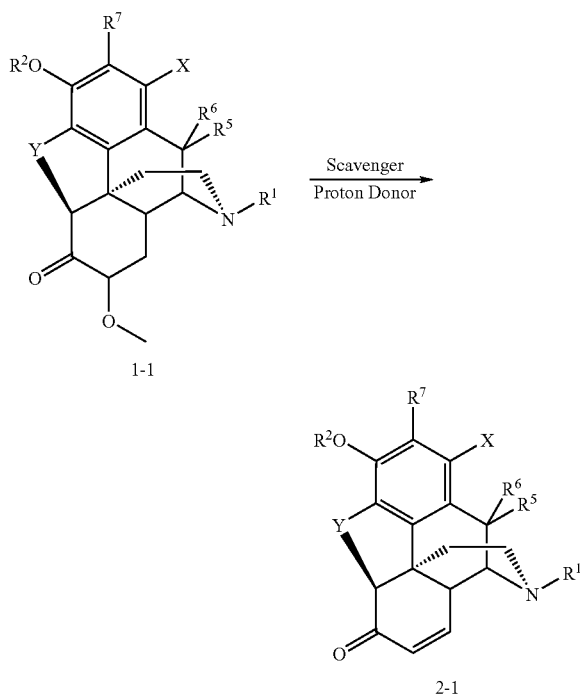

wherein: R$^1$, R$^2$, R$^5$, R$^6$, R$^7$, X, and Y are as defined above in Reaction Scheme 1.

In the process, compound 1-1 is contacted with an alcohol scavenger. The alcohol may be an alcohol having from about 1 to about 8 carbon atoms. In an exemplary embodiment, the alcohol scavenger is a methanol scavenger. Suitable methanol scavengers include P$_2$O$_5$, POCl$_3$, POBr$_3$, PCl$_3$, PBr$_3$, SOCl$_2$, SOBr$_2$, MeSO$_2$Cl, (MeSO$_2$)$_2$O, SO$_3$, (CF$_3$SO$_2$)$_2$O, (CF$_3$CO)$_2$O, (CR$_3$CO)$_2$O, and R$^3$SiX (wherein X is Cl or Br, and R$^3$ is an alkyl group).

To facilitate the reaction of compound 1-1 with the alcohol scavenger, the reaction is generally carried out in the presence of a proton donor. The proton donor generally has a PKa less than about 0. Suitable proton donors having this characteristic include, but are not limited to MeSO$_3$H, poly H$_3$PO$_4$, H$_3$PO$_4$, H$_2$SO$_4$, HCl, HBr, HClO$_4$, HI, HNO$_3$, CF$_3$SO$_3$H, toluenesulfonic acid, HClO$_3$, HBrO$_4$, HIO$_3$, and HIO$_4$.

The molar ratio of compound 1-1 to proton donor to alcohol scavenger is typically from about 1:0.5:2 to about 1:2:20. In an exemplary embodiment, the molar ratio of compound 4 to alcohol scavenger is typically from about 1:1:2 to about 1:2:8.

The reaction is generally conducted in the presence of an aprotic solvent. Non-limiting examples of aprotic solvents include ether solvents, acetonitrile, benzene, N,N-dimethylformamide (DMF), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), N,N-dimethylacetamide (DMAC), N-methylpyrrolidinone (NMP), ethyl acetate, n-propyl acetate, ethyl formate, ethyl methyl ketone, formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), toluene, trichloromethane. The weight ratio of compound 1-1 to aprotic solvent(s) may range from about 1:3 to about 1:50.

The temperature of the reaction mixture for the formation of compound 2-1 from 1-1 will typically be within the range of about 20° C. to about 120° C. More typically, the reaction will be carried out at a temperature between about 20° C. and about 45° C. The reaction is preferably performed under ambient pressure, and preferably in an inert atmosphere (e.g., nitrogen or argon).

(i) Preparation from Compound 2-1(a)

In another embodiment, the substrate for preparation of compound 2-1 corresponds to compound 2-1(a) depicted in accordance with the following Reaction Scheme:

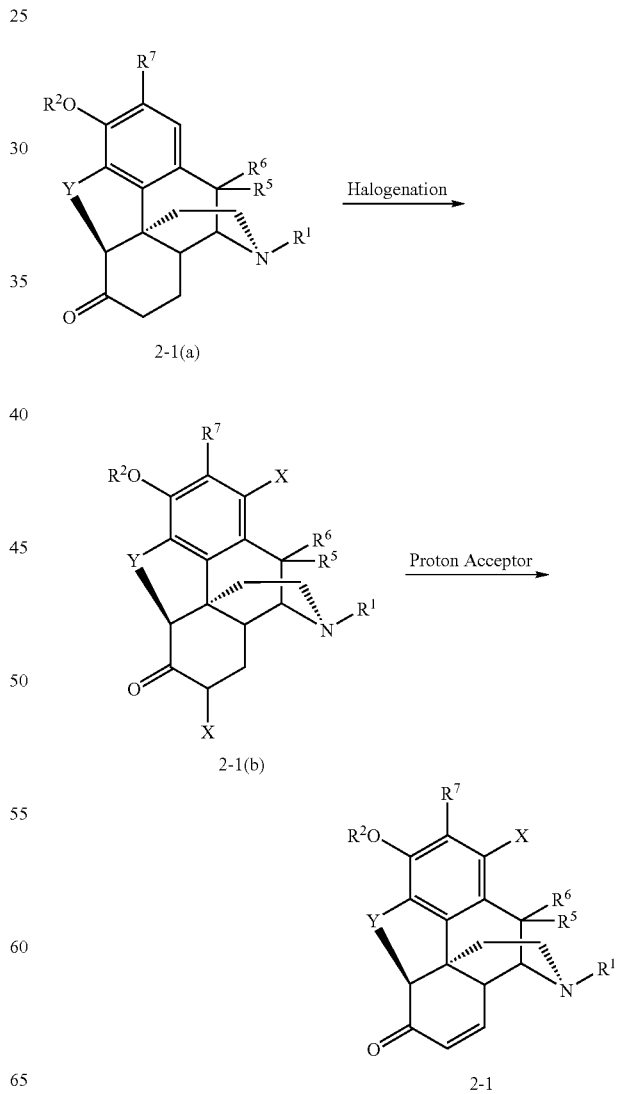

wherein: $R^1$, $R^2$, $R^5$, $R^6$, $R^7$, X, and Y are as defined above in Reaction Scheme 1. In a preferred iteration, the halogen, X, is bromide.

Typically, the halogenation reaction is conducted in the presence of an organic solvent. Suitable organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methyltetrahydrofuran, pentyl acetate, n-propyl acetate, tetrahydrofuran, toluene, combinations thereof, and the like. The weight ratio of compound 2-1(a) to solvent can and will vary without departing from the scope of the invention. For example, the weight ratio may range from about 1:5 to 1:20.

The molar ratio of compound 2-1(a) to halogen (e.g., bromide) may range from about 1:2 to about 1:10. In an exemplary embodiment, the molar ratio of compound 2-1(a) to halogen is about 1:2.

The halogenation reaction will typically be within the range of about −40° C. to about 20° C. More typically, the reaction will be carried out at a temperature between about −35° C. and about 10° C. The reaction is preferably performed under ambient pressure, and preferably in an inert atmosphere (e.g., nitrogen or argon).

The reaction involving the conversion of compound 2-1(b) to compound 2-1 is carried out in the presence of a proton acceptor and an aprotic solvent. Suitable aprotic solvents are as described above. In general, the proton acceptor has a pKa of between about 7 and about 13, preferably between about 8 and about 10. Representative proton acceptors that may be employed include, but are not limited to, borate salts (such as, for example, $NaBO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N-dimethylaminopyddine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl)ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino] ethanesulfonic acid (TES), salts and/or mixtures thereof, and the like), and combinations thereof. The molar ratio of compound 2-1(b) to proton acceptor is from about 1:1 to about 1:10. In an exemplary iteration, the molar ratio of compound 2-1(b) to proton acceptor is from about 1:5 to about 1:10.

The temperature for the conversion of compound 2-1(b) to 2-1, will typically be within the range of about 80° C. to about 140° C. More typically, the reaction will be carried out at a temperature between about 115° C. and about 125° C. The reaction is preferably performed under ambient pressure, and preferably in an inert atmosphere (e.g., nitrogen or argon).

(b) Step A: Conversion of Compound 2-1 to Compound 3-1

The substrate for preparation of compound 3-1 corresponds to compound 2-1 depicted in Reaction Scheme 1. As detailed above, compound 2-1 may be made via a variety of synthetic routes in accordance with an aspect of the invention.

In Step A of the process, compound 2-1 is typically contacted with $(R^3CO)_2O$ in the presence of a weak proton acceptor having formula $R^3CO_2M$, wherein $R^3$ is a hydrocarbyl or a substituted hydrocarbyl, and M is a metal atom selected from the group consisting of Li, Na, and K. Exemplary hydrocarbyl groups for $R^3$ include alkyl substituted alkyl, aryl, and substituted aryl. In an exemplary embodiment, $(R^3CO)_2O$ is acetic anhydride and the weak proton acceptor is sodium acetate.

The molar ratio of compound 2-1 to $(R^3CO)_2O$ is typically from about 1:2 to about 1:20. In an exemplary embodiment, the molar ratio of compound 2-1 to $(R^3CO)_2O$ is typically from about 1:3 to about 1:6.

The reaction is generally conducted in the presence of an aprotic solvent. Suitable aprotic solvents are as described herein. The weight ratio of compound 2-1 to aprotic solvent(s) may range from about 1:3 to about 1:50.

The temperature of the reaction mixture for Step A of the process will typically be within the range of about 50° C. to about 110° C. More typically, the reaction will be carried out at a temperature between about 80° C. and about 100° C. The reaction is preferably performed under ambient pressure, and preferably in an inert atmosphere (e.g., nitrogen or argon).

(c) Step B: Conversion of Compound 3-1 to Compound 4-1

The substrate for preparation of compound 4-1 corresponds to compound 3-1 depicted in Reaction Scheme 1.

In Step B of the process, compound 3-1 is typically contacted with an oxidizing agent. In an exemplary embodiment, the oxidizing agent comprises an agent selected from the group consisting of $RZCO_3H$, $RZCO_2H/H_2O_2$, and $RZCO_2H$/other oxidants, wherein $R^Z$ is selected from the group consisting of alkyl, substituted alkyl, aryl, and substituted aryl. Exemplary oxidizing agents include $CH_3CO_3H$ and $m\text{-}Cl\text{-}Ph\text{-}CO_3H$.

The molar ratio of compound 3-1 to oxidizing agent is typically from about 1:1 to about 1:2. In an exemplary embodiment, the molar ratio of compound 3-1 to oxidizing agent is typically from about 1:1 to about 1:1.2.

The reaction is generally conducted in the presence of a protic solvent, typically in a combination of water and acetic acid. The solvent may alternatively, or additionally, comprise other protic solvents such as alcohol or other water-miscible solvent; thus, for example, the protic solvent may be water, a water/alcohol mixture, or a water/water-miscible solvent mixture. Representative alcohols for the water/alcohol mixture include, for example, methanol, ethanol, isopropyl alcohol, isobutyl alcohol, t-butyl alcohol, n-propyl alcohol, n-butyl alcohol, and combinations thereof. Other water-miscible solvents for the water/water-miscible solvent mixture include, for example, acetonitrile, N,N-dimethylformamide, 1-methyl-2-pyrrolidinone, N,N-dimethylacetamide, acetone, tetrahydrofuran, and combinations thereof. The weight ratio of compound 3-1 to protic solvent(s) may range from about 1:1 to about 1:20.

The temperature of the reaction mixture for Step B of the process will typically be within the range of about 0° C. to about 100° C. More typically, the reaction will be carried out at a temperature between about 10° C. and about 45° C. The reaction is preferably performed under ambient pressure, and preferably in an inert atmosphere (e.g., nitrogen or argon).

(d) Step C: Conversion of Compound 4-1 to Compound 5-1

The substrate for preparation of compound 5-1 corresponds to compound 4-1 depicted in Reaction Scheme 1.

In Step C of the process, compound 4-1 is reduced by catalysis to form compound 5-1. Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. In an exemplary embodiment, compound 6 is reduced using catalytic reduction (e.g., Pd/C catalyzed transfer hydrogenation). Preferred catalysts include transition metal catalysts selected from the group consisting of Pd/C, PVC, Ru/C, and Rh/C.

The molar ratio of compound 4-1 to metal catalyst is typically from about 1:0.0005 to about 1:0.005. In an exemplary embodiment, the molar ratio of compound 4-1 to transition metal catalyst is typically from about 1:0.0008 to about 1:0.0015.

The reaction is generally conducted in the presence of an aprotic solvent. Suitable aprotic solvents are as described herein. The weight ratio of compound 4-1 to aprotic solvent(s) may range from about 1:1 to about 1:20.

The temperature of the reaction mixture for Step C of the process will typically be within the range of about 20° C. to about 120° C. More typically, the reaction will be carried out at a temperature between about 50° C. and about 85° C. The reaction is preferably performed under pressurized hydrogen. Generally, the hydrogen pressure is between about 0 and about 500 PSI, and more preferably, between about 20 and about 60 PSI.

(e) Step D: Conversion of Compound 5-1 to Compound 6-1

The substrate for preparation of compound 6-1 corresponds to compound 5-1 depicted in Reaction Scheme 1.

In Step D of the process, compound 5-1 is typically N-demethylated with an agent selected from hydrocarbylhaloformates or N,N-dihydrocarbylhaloformamides. Mixtures of hydrocarbylhaloformates or mixtures of N,N-dihydrocarbylhaloformamides and at least one hydrocarbylhaloformate may also be employed. In one embodiment, the demethylating agent is a hydrocarbylhaloformate having the formula L-C(O)OZ, wherein L is halogen and Z is hydrocarbyl or substituted hydrocarbyl. Preferably, the halogen substituent, L, is bromo, chloro, fluoro, or iodo. More preferably, L is chloro or bromo, and in one embodiment, L is chloro. Although Z may be selected from hydrocarbyl or substituted hydrocarbyl, in one embodiment Z is alkyl, substituted alkyl, alkenyl, substituted alkenyl, aryl, substituted aryl, alkylaryl, or substituted alkylaryl. Thus, the demethylating agent may be, for example, an alkyl haloformate, an aryl haloformate, an aralkyl hydrocarbylhaloformate, or a mixture thereof. In one preferred embodiment, Z is alkyl, alkenyl, aryl, aralkyl, or alkyl substituted with one or more of halo, cycloalkyl, phenyl, or substituted phenyl. By way of further example, Z may be methyl, ethyl, propyl, isopropyl, butyl, isobutyl, tert-butyl, phenyl, benzyl, methoxymethyl, vinyl, 1-chloroethyl, or 2-chlomethyl. Typically, the N-demethylating agent will be selected from $C_{1-8}$alkyl chloroformates (e.g., $C_1$ to $C_8$ alkyl), phenyl chloroformate, benzyl chloroformate, and combinations thereof.

To facilitate the N-demethylation of compound 5-1, the reaction is carried out in the presence of a proton acceptor. In general, the proton acceptor has a pKa of between about 7 and about 13, preferably between about 8 and about 10. Representative proton acceptors that may be employed include, but are not limited to, borate salts (such as, for example, $NaBO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl) piperazine-1-ethanesulfonic acid (HEPES), 2-(4-morpholinyl)ethanesulfonic acid (MES), 4-Page 16 of 54 morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. Where the proton acceptor is an organic buffer, the organic buffer preferably lacks a hydroxy-substituted nitrogen atom, as this substituent may compete for reaction with the haloformate reactant. In one embodiment, the proton acceptor is selected from the group consisting of $NaHCO_3$, $KHCO_3$, $K_2CO_3$, NaOH, KOH, and mixtures thereof. In a preferred embodiment, the proton acceptor is $NaHCO_3$ or $KHCO_3$ or a combination thereof.

To minimize the formation of byproducts, the demethylating agent is preferably maintained in relatively low concentration relative to compound 5-1. In a batch reaction, for example, this can be achieved by incremental addition of the demethylating agent to a reaction mixture containing compound 5-1. Regardless of whether the reaction is carried out in a batch, continuous, or semi-continuous mode, it is generally preferred that the molar ratio of compound 5-1 to N-demethylating agent to proton acceptor is from about 1:2:1 to about 1:20:20. In an exemplary embodiment, the molar ratio of compound 5-1 to N-demethylating agent to proton acceptor is from about 1:6:4 to about 1:15:10.

The demethylation reaction is generally conducted in the presence of an aprotic solvent. Suitable aprotic solvents are as herein. The weight ratio of compound 5-1 to aprotic solvent(s) may range from about 1:1 to about 1:20.

The temperature of the reaction mixture for Step D of the process will typically be within the range of about 50° C. to about 120° C. More typically, the reaction will be carried out at a temperature between about 50° C. and about 80° C. The reaction is preferably performed under ambient pressure, and preferably in an inert atmosphere (e.g., nitrogen or argon).

(f) Step E: Conversion of Compound 6-1 to Compound 7-1

The substrate for preparation of compound 7-1 corresponds to compound 6-1 depicted in Reaction Scheme 1. Compound 6-1 may be converted to 7-1 via two discrete synthetic routes. In one route, compound 6-1 is combined with a proton donor. Alternatively, in the other route 6-1 is contacted with an O-demethylating agent.

(i) Proton Donor

In one embodiment for Step E of the process, compound 6-1 is contacted with a proton donor. The proton donor generally has a PKa less than about O, Suitable proton donors having this characteristic include, but are not limited to MeSO$_3$H, poly H$_3$PO$_4$, H$_3$PO$_4$, H$_2$SO$_4$, HCl, HBr, HClO$_4$, HI, HNO$_3$, CF$_3$SO$_3$H, toluenesulfonic acid, HClO$_3$, HBrO$_4$, HIO$_3$, and HIO$_4$. In an exemplary embodiment, the proton donor will comprise bromide.

The molar ratio of compound 6-1 to proton donor is typically from about 1:3 to about 1:20. In an exemplary embodiment, the molar ratio of compound 6-1 to proton donor is typically from about 1:3 to about 1:10.

The reaction is generally conducted in the presence of a protic solvent. Water is an example of a suitable protic solvent. The solvent may alternatively, or additionally, comprise other protic solvents such as alcohol or other water-miscible solvent; thus, for example, the protic solvent may be water, a water/alcohol mixture, or a water/water-miscible solvent mixture. Representative alcohols for the water/alcohol mixture include, for example, methanol, ethanol, isopropyl alcohol, isobutyl alcohol, t-butyl alcohol, n-propyl alcohol, n-butyl alcohol, and combinations thereof. Other water-miscible solvents for the water/water-miscible solvent mixture include, for example, acetonitrile, N,N-dimethylformamide, 1-methyl-2-pyrrolidinone, N,N-dimethylacetamide, acetone, tetrahydrofuran, and combinations thereof. The weight ratio of compound 6-1 to protic solvent is generally within the range of about 1:1 to about 1:20.

In this aspect of Step E of the process, the temperature of the reaction mixture will typically be within the range of about 80° C. to about 120° C. More typically, the reaction will be carried out at a temperature between about 90° C. and about 105° C. The reaction is preferably performed under ambient pressure, and preferably in an inert atmosphere (e.g., nitrogen or argon).

(ii) O-demethylation

In another embodiment for Step E of the process, compound 6-1 is contacted with an O-demethylating agent. Suitable O-demethylating agents include, for example, BBr$_3$.

For the O-demethylation reaction, the molar ratio of compound 6-1 to O-demethylating agent is typically from about 1:2 to about 1:6. In an exemplary embodiment, the molar ratio of compound 6-1 to O-demethylating agent is typically from about 1:2 to about 1:4.

The reaction is generally conducted in the presence of an aprotic solvent. Suitable aprotic solvents are as described in herein. In general, the weight ratio of compound 6-1 to aprotic solvent is within the range of about 1:2 to 1:30.

For this aspect of Step E of the process, the temperature of the reaction mixture will typically be within the range of about –10° C. to about 45° C. More typically, the reaction will be carried out at a temperature between about 0° C. and about 25° C. The reaction is preferably performed under ambient pressure, and preferably in an inert atmosphere (e.g., nitrogen or argon).

(g) Step F: Conversion of Compound 7-1 to Compound 8-1

The substrate for preparation of compound 8-1 corresponds to compound 7-1 depicted in Reaction Scheme 1.

In Step F of the process, compound 7-1 is typically contacted with $R^{1a}X$, wherein $R^{1a}$ is a hydrocarbyl or a substituted hydrocarbyl, and X is a halogen. Included among some of the more preferred hydrocarbyl groups for $R^{1a}$ are methyl, ethyl, propyl, isopropyl, butyl, isobutyl, tertiary butyl, pentyl, {CH$_2$}-cyclopropyl, {CH$_2$}-vinyl, {CH$_2$}-cyclobutyl, {CH$_2$}-cyclopentyl, {CH$_2$}-cyclohexyl, {CH$_2$}-phenyl, methylphenyl, or {CH$_2$}-benzyl. For each of the foregoing embodiments, an exemplary X is bromide.

The molar ratio of compound 7-1 to $R^{1a}X$ is typically from about 1:1 to about 1:2. In an exemplary embodiment, the molar ratio of compound 7-1 to $R^{1a}X$ is typically from about 1:1 to about 1:1.3

For Step F of the process, the solvent preferably includes an organic solvent. Representative organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methyltetrahydrofuran, pentyl acetate, n-propyl acetate, tetrahydrofuran, toluene, combinations thereof, and the like.

In addition to the organic solvent, the solvent system may additionally contain an aprotic solvent. Suitable aprotic solvents are as described herein. The weight ratio of compound 7-1 to solvent(s) will generally be within the range of 1:2 to 1:10.

The temperature of the reaction mixture for Step F of the process will typically be within the range of about 20° C. to about 120° C. More typically, the reaction will be carried out at a temperature between about 60° C. and about 80° C. The reaction is preferably performed under ambient pressure, and preferably in an inert atmosphere (e.g., nitrogen or argon).

As will be appreciated by a skilled artisan, the yield and purity of compound 8-1 produced by the process can and will vary depending upon the particular reactants and reaction parameters selected. For the overall reaction, i.e. from compound 1 to compound 8-1, the yield will generally range from about 5% to greater than about 45%. The purity will generally range from about 90% to greater than about 99% as determined by chromatography (e.g., HPLC), more typically, the purity will be greater than about 98%.

The product formed by Step F, compound 8, may have the following substituents:

$R^{1a}$ is selected from the group consisting of hydrocarbyl, and substituted hydrocarbyl;

$R^2$ is selected from the group consisting of methyl and hydrogen;

$R^5$, and $R^6$ are independently selected from the group consisting of hydrogen, halogen, hydroxyl, NH$_2$, SH, hydrocarbyl, and substituted hydrocarbyl, wherein $R^5$, and $R^6$ may together form a group selected from the group consisting of =O, and =S;

$R^7$ is selected from the group consisting of hydrogen, halogen, hydroxyl, NH$_2$, CN, hydrocarbyl, and substituted hydrocarbyl;

Y is selected from the group consisting of oxygen, sulfur and nitrogen.

Included among some of the more preferred hydrocarbyl groups for $R^{1a}$, are methyl, ethyl, propyl, isopropyl, butyl, isobutyl, tertiary butyl, pentyl, {—}CH$_2$-cyclopropyl, {CH$_2$}-vinyl, {—}CH$_2$-cyclobutyl, {—}CH$_2$ cyclopentyl, {—}CH$_2$-cyclohexyl, {—}CH$_2$-phenyl, {—}CH$_2$-methylphenyl, or {—}CH$_2$-benzyl.

Compounds corresponding to compound 8 are generally (+)-nal morphinans and may be end products themselves, or intermediates that may be further derivatized in one or more steps to yield further nal morphinan intermediates or end products. By way of non-limiting example, one or more compounds corresponding to compound 8 may be used in processes to produce a compound selected from the group consisting of (+)-naloxone, (+)-naltrexone, (+)-3-O-methyl naltrexone, (+)-norhydrocodone, (+)-norhydromorphone, (+)-noroxymorphone, (+)-noroxycodone, (+)-naltrexol, (+)-naloxol, (+)-naltrexone methobromide, (+)-naltrexol methobromide and the salts, intermediates, and analogs thereof. General reaction schemes for the preparation of such commercially valuable nal morphinans are disclosed, among other places, in U.S. Pat. No. 4,368,326 to Rice, the entire disclosure of which is hereby incorporated by reference herein.

The process for the preparation of compound 8-1 may be used to produce compounds that have either a (−) or (+) stereochemistry configuration, with respect to the rotation of polarized light. More specifically, each chiral center may have an R or an S configuration. For ease of discussion, the ring atoms of the core morphinan structure referenced herein are numbered as follows:

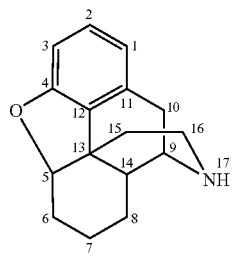

As illustrated in the core morphinan structure, there are four chiral carbons comprising any of the compounds utilized in the process of the invention (i.e., compound 1, 2, or 3), i.e., carbons 5, 13, 14, and 9. Thus, the configuration of compounds 1, 2, or 3 may be RRRR, RRRS, RRSR, RSSS, SRRR, SRRS, SRSR, SRSS, RSRR, RSRS, RSSR, RSSS, SSRR, SSRS, SSSR, or SSSS, with respect to C5, to C13, C14, and C9, provided that the C15 and the C16 atoms are both either on the alpha face of the molecule or the beta face of the molecule.

The invention also encompasses salts of any of the above-described compounds. Exemplary salts include without limitation hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

(II) Preparation of Intermediates Compounds

Another aspect of the present invention encompasses synthetic routes for producing compounds that may be used as intermediates in the preparation of (+)-nal morphinans. For example, several of the intermediates described below are used in the process for preparing (+)-nal morphinans illustrated in Reaction Scheme 1 (depicted in (I)), and Reaction Scheme 2 (shown in the Examples) below.

(a) Conversion of Compound 1 to Compound 2

In general compounds 1 and 2 are intermediates utilized in Steps A and B of Reaction Schemes 1 and 2 described herein. It is also envisioned that these intermediate compounds may be beneficially used in other synthetic routes to produce nal morphinans. Briefly, in the process compound 1 may be contacted with an alcohol scavenger in the presence of a proton donor to form compound 2 according to the following reaction scheme:

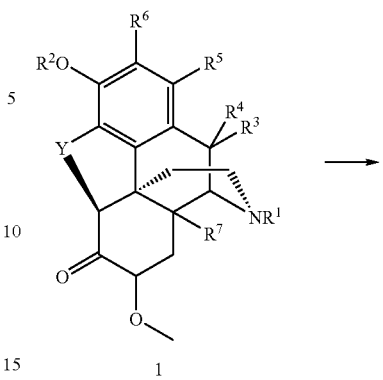

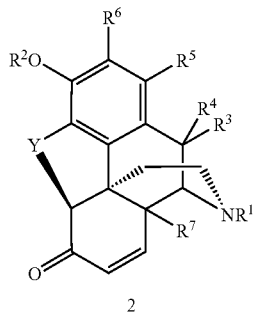

wherein:
R$^1$ and R$^2$ are independently selected from the group consisting of hydrogen, hydrocarbyl, substituted hydrocarbyl, and a protecting group;

R$^3$, and R$^4$ are independently selected from the group consisting of hydrogen, halogen, hydroxyl, NH$_2$, SH, hydrocarbyl, and substituted hydrocarbyl, wherein R$^3$, and R$^4$ may together form a group selected from the group consisting of =O, and =S;

R$^5$, and R$^6$ are independently selected from the group consisting of hydrogen, halogen, hydroxyl, NH$_2$, CN, hydrocarbyl, and substituted hydrocarbyl;

R$^7$ is selected from the group consisting of hydrogen and hydroxyl; and

Y is selected from the group consisting of oxygen, sulfur, and nitrogen.

Suitable reactants and reaction conditions are generally known in the art or as described for Step A of Reaction Scheme 1.

(b) Conversion of Compound 2 to Compound 3

In general, compounds 2 and 3 are intermediates utilized in Steps B and C of Reaction Schemes 1 and 2 described herein. It is also envisioned that these intermediate compounds may be beneficially used in other synthetic routes to produce nal morphinans. Briefly, in the process compound 2 may be contacted with (R$^0$CO)$_2$O in the presence of R$^7$CO$_2$M to form compound 3 according to the following reaction scheme:

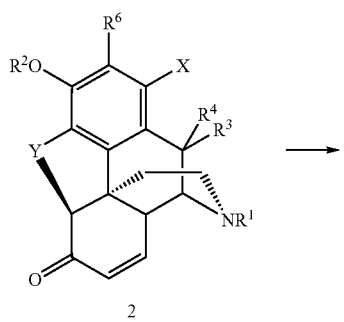

2

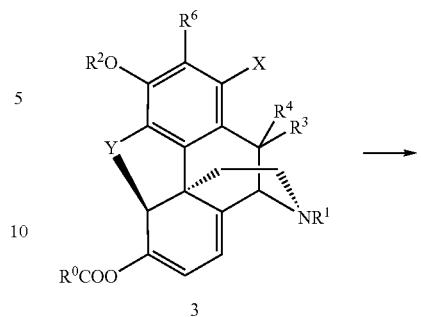

3

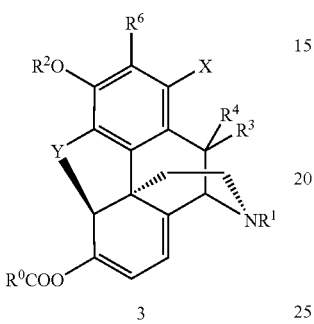

3

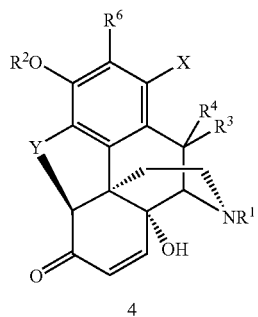

4

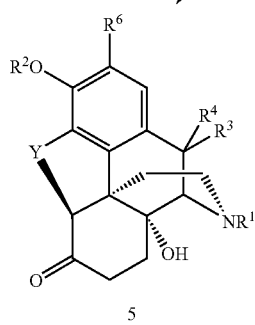

5 wherein:
- $R^0$ is selected from the group consisting of alkyl, substituted alkyl, aryl, and substituted aryl;
- $R^1$ and $R^2$ are independently selected from the group consisting of hydrogen, hydrocarbyl, substituted hydrocarbyl, and a protecting group;
- $R^3$, and $R^4$ are independently selected from the group consisting of hydrogen, halogen, hydroxyl, $NH_2$, SH, hydrocarbyl, and substituted hydrocarbyl, wherein $R^3$, and $R^4$ may together form a group selected from the group consisting of =O, and =S;
- $R^6$ is selected from the group consisting of hydrogen, halogen, hydroxyl, $NH_2$, CN, hydrocarbyl, and substituted hydrocarbyl;
- $R^7$ is selected from the group consisting of hydrocarbyl or substituted hydrocarbyl;
- M is a metal atom selected from the group consisting of Li, Na, and K;
- X is selected from the group consisting of halogen and hydrogen; and
- Y is selected from the group consisting of oxygen, sulfur, and nitrogen.

Suitable reactants and reaction conditions are generally known in the art or as described for Step B of Reaction Scheme 1.

(c) Conversion of Compound 3 to Compound 4 to Compound 5

In general, compounds 3, 4, and 5 are intermediates utilized in Steps C, D and E of Reaction Schemes 1 and 2 described herein. It is also envisioned that these intermediate compounds may be beneficially used in other synthetic routes to produce nal morphinans. Briefly, in the process compound 3 may be contacted with an oxidizing agent to form compound 4. Compound 4 is then reduced to form compound 5 according to the following reaction scheme:

wherein:
- $R^0$ is selected from the group consisting of alkyl, substituted alkyl, aryl, and substituted aryl;
- $R^1$ and $R^2$ are independently selected from the group consisting of hydrogen, hydrocarbyl, substituted hydrocarbyl, and a protecting group;
- $R^3$, and $R^4$ are independently selected from the group consisting of hydrogen, halogen, hydroxyl, $NH_2$, SH, hydrocarbyl, and substituted hydrocarbyl, wherein $R^3$, and $R^4$ may together form a group selected from the group consisting of =O, and =S;
- $R^6$ is selected from the group consisting of hydrogen, halogen, hydroxyl, $NH_2$, CN, hydrocarbyl, and substituted hydrocarbyl;
- X is selected from the group consisting of halogen and hydrogen; and
- Y is selected from the group consisting of oxygen, sulfur, and nitrogen.

Suitable reactants and reaction conditions are generally known in the art or as described for Steps C and D of Reaction Scheme 1.

(d) Conversion of Compound 5a to Compound 6

In general, compounds 5a and 6 are intermediates utilized in Steps E and F of Reaction Schemes 1 and 2 described herein. It is also envisioned that these intermediate compounds may be beneficially used in other synthetic routes to produce nal morphinans. Briefly, in the process compound 5a may be contacted with an N-demethylating agent in the presence of a proton acceptor to form compound 6 according to the following reaction scheme:

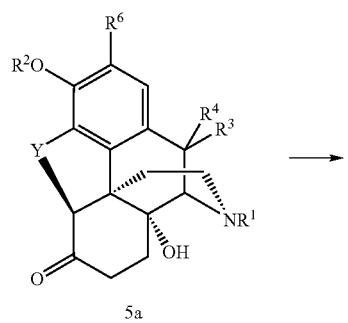

5a

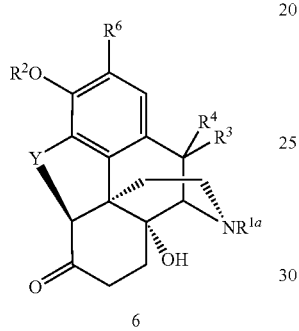

6 wherein:

$R^{1a}$ is {—}$OCOR^{3a}$;

$R^1$ is methyl;

$R^2$ is selected from the group consisting of hydrogen, hydrocarbyl, substituted hydrocarbyl, and a protecting group;

$R^{3a}$ is selected from the group consisting of hydrocarbyl, and substituted hydrocarbyl;

$R^3$, and $R^4$ are independently selected from the group consisting of hydrogen, halogen, hydroxyl, $NH_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, $NH_2$, CN, hydrocarbyl, and substituted hydrocarbyl; and Y is selected from the group consisting of oxygen, sulfur, and nitrogen.

Suitable reactants and reaction conditions are generally known in the art or as described for Step E of Reaction Scheme 1.

(e) Conversion of Compound 6a to Compound 7

In general, compounds 6a and 7 are intermediates utilized in Steps F and G of Reaction Schemes 1 and 2 described herein. It is also envisioned that these intermediate compounds may be beneficially used in other synthetic routes to produce nal morphinans. Briefly, in the process compound 6a may be contacted with a proton donor to form compound 7 according to the following reaction scheme:

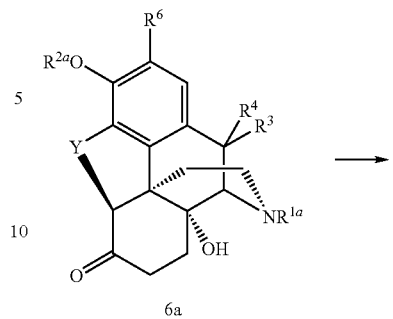

6a

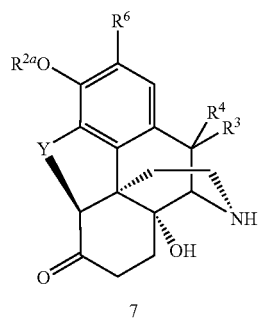

7 wherein:

$R^{1a}$ is {—}$OCOR^{3a}$;

$R^{2a}$ is selected from the group consisting of hydrogen, alkyl, substituted alkyl, aryl, substituted aryl, and acyl;

$R^{3a}$ is hydrocarbyl, and substituted hydrocarbyl;

$R^3$, and $R^4$ are independently selected from the group consisting of hydrogen, halogen, hydroxyl, $NH_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, $NH_2$, CN, hydrocarbyl, and substituted hydrocarbyl; and Y is selected from the group consisting of oxygen, sulfur, and nitrogen.

Suitable reactants and reaction conditions are generally known in the art or as described for Step F of Reaction Scheme 1.

(f) Conversion of Compound 6a to Compound 7a

In general, compounds 6a and 7a are intermediates utilized in Steps F and G of Reaction Schemes 1 and 2 described herein. It is also envisioned that these intermediate compounds may be beneficially used in other synthetic routes to produce nal morphinans. Briefly, in the process compound 6a may be contacted with an agent selected from a proton donor and an O-demethylating agent to form compound 7a according to the following reaction scheme:

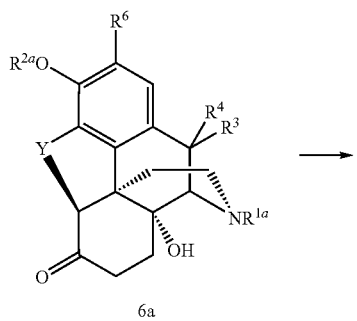

6a

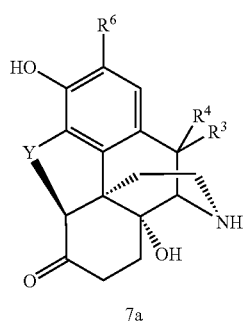

7a wherein:

$R^{1a}$ is {—}OCOR$^{3a}$;

$R^{2a}$ is selected from the group consisting of hydrogen, alkyl, substituted alkyl, aryl, substituted aryl, and acyl;

$R^{3a}$ is hydrocarbyl, and substituted hydrocarbyl;

$R^3$, and $R^4$ are independently selected from the group consisting of hydrogen, halogen, hydroxyl, NH$_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, NH$_2$, CN, hydrocarbyl, and substituted hydrocarbyl; and Y is selected from the group consisting of oxygen, sulfur, and nitrogen.

Suitable reactants and reaction conditions are generally known in the art or as described for Step F of Reaction Scheme 1.

(g) Conversion of Compound 7 to Compound 8

In general, compounds 7 and 8 are intermediates utilized in Step G of Reaction Schemes 1 and 2 described herein. It is also envisioned that these intermediate compounds may be beneficially used in other synthetic routes to produce nal morphinans. Briefly, in the process compound 7 may be contacted with $R^1X$ to form compound 8 according to the following reaction scheme:

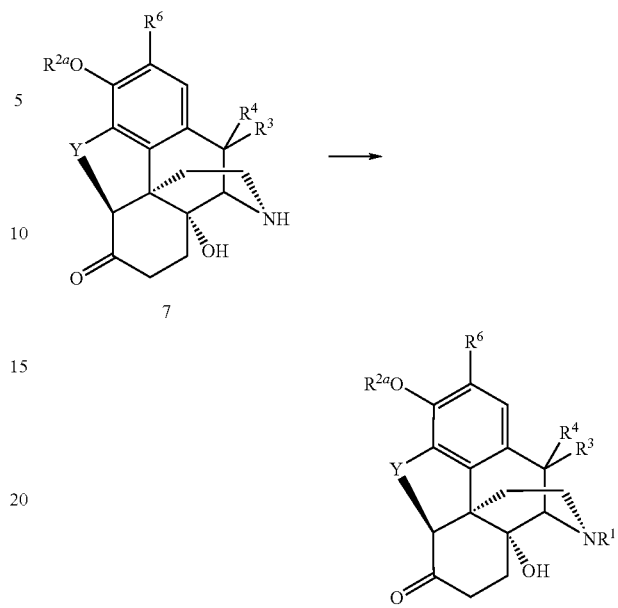

wherein:

$R^1$ is selected from the group consisting of hydrocarbyl, and substituted hydrocarbyl;

$R^{2a}$ is selected from the group consisting of hydrogen, alkyl, substituted alkyl, aryl, substituted aryl, and acyl;

$R^3$, and $R^4$ are independently selected from the group consisting of hydrogen, halogen, hydroxyl, NH$_2$, SH, hydrocarbyl, and substituted hydrocarbyl, wherein $R^3$, and $R^4$ may together form a group selected from the group consisting of =O, and =S;

$R^6$ is selected from the group consisting of hydrogen, halogen, hydroxyl, NH$_2$, CN, hydrocarbyl, and substituted hydrocarbyl;

X is a halogen; and

Y is selected from the group consisting of oxygen, sulfur, and nitrogen.

Suitable reactants and reaction conditions are generally known in the art or as described for Step G of Reaction Scheme 1.

DEFINITIONS

The term "acyl," as used herein alone or as part of another group, denotes the moiety formed by removal of the hydroxy group from the group COOH of an organic carboxylic acid, e.g., RC(O)—, wherein R is R$_1$, R$_1$O—, R$_1$R$_2$N—, or R$_1$S—, R$_1$ is hydrocarbyl, heterosubstituted hydrocarbyl, or heterocyclo, and R$_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alcohol scavenger" as used herein is a reagent that can react with an alcohol and release an acid at the same time.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkaryl" or "alkylaryl" as used herein describes groups which are preferably aryl groups having a lower alkyl substituent, such as toluoyl, ethylphenyl, or methylnapthyl.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aralkyl" as used herein describes groups which are preferably lower alkyl containing from one to eight carbon atoms having an aryl substituent, such as benzyl, phenylethyl, or 2-napthylmethyl.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various iterations of the synthetic routes for producing (+)-nal morphinans described herein.

Example 1

Production of (+)-Naltrexone from (+)-7-Methoxyhydrocodone

Reaction Scheme 2 depicts the production of (+)-naltrexone from (+)-7-methoxyhydrocodone according to one aspect of the invention:

Reaction Scheme 2

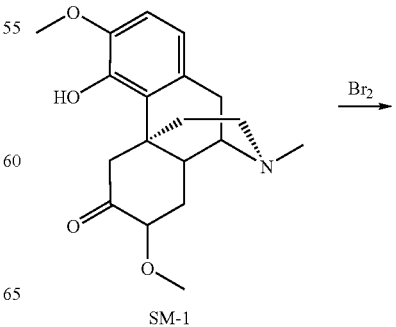

SM-1

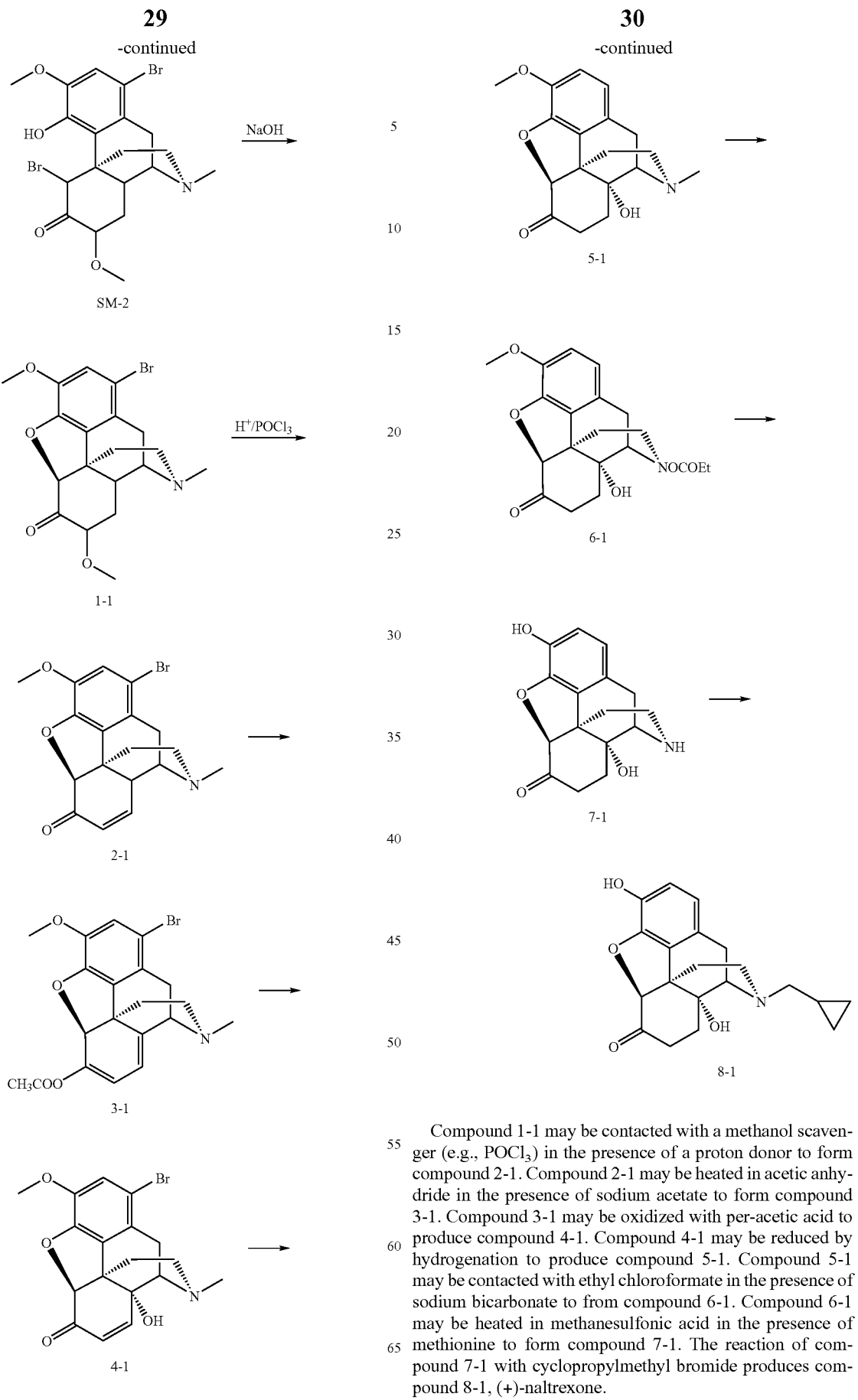

Compound 1-1 may be contacted with a methanol scavenger (e.g., POCl₃) in the presence of a proton donor to form compound 2-1. Compound 2-1 may be heated in acetic anhydride in the presence of sodium acetate to form compound 3-1. Compound 3-1 may be oxidized with per-acetic acid to produce compound 4-1. Compound 4-1 may be reduced by hydrogenation to produce compound 5-1. Compound 5-1 may be contacted with ethyl chloroformate in the presence of sodium bicarbonate to from compound 6-1. Compound 6-1 may be heated in methanesulfonic acid in the presence of methionine to form compound 7-1. The reaction of compound 7-1 with cyclopropylmethyl bromide produces compound 8-1, (+)-naltrexone.

Examples 2-13

Detail the Production of (+)-Naltrexone from (+)-Hydrocodone

Example 2

Synthesis of (+)-1,7-Dibromohydrocodone from (+)-Hydrocodone 1,7-Dibromohydrocodone was produced from hydrocodone according to the following scheme:

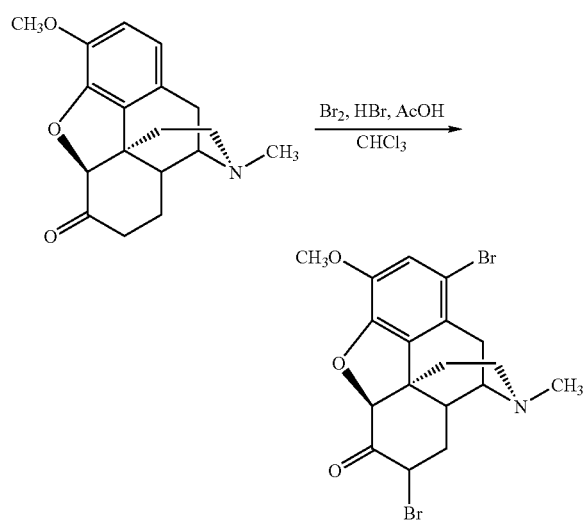

(+)-Hydrocodone (4.0 g, 12.67 mmol) was dissolved in chloroform (50 mL) in a 250 mL three neck RB flask under a blanket of nitrogen. To this stirred solution was added 2 mL of a 33% HBr solution in acetic acid. The resulting mixture was stirred and cooled to −35° C., forming a dark green solution. To this solution was slowly added a pre-mixed solution of 1.5 mL bromine in 20 mL of chloroform using a dropping funnel over a period of 1.5 hours. Approximately half-way through addition, stirring efficiency was decreased due to solid particle build-up, but the solids dissolved as the addition continued. The resultant dark reddish-brown slurry was warmed to −5° C., then to 0° C. over a period of one hour. The reaction temperature was then maintained between 0° C. and 10° C. until HPLC indicated that the reaction was complete. $NaS_2O_5$ (0.4 g) was then added, and the organic phase was separated. The solvents were removed in vacuo to give approximately 80% pure crude product before recrystallization.

Trial 2. Crude (+)-hydrocodone (3.3 g, ~90%) was dissolved in chloroform (50 mL), and 5 mL of 33% HBr in HOAc was added. After 40 mL of acetic acid was added, the reaction mixture was cooled down to −20° to −30° C. and maintained at that temperature. The reaction flask was flushed with nitrogen and the reaction was dept under nitrogen throughout the reaction. A solution of bromine (1.25 mL, 2.1 eq) in chloroform (20 mL) was added to the reaction mixture over 30 min. The reaction mixture was allowed to warm up to 0-5° C. and was stirred at 0-5° C. for 5 h (the reaction was complete shown by HPLC analysis). Sodium metabissulfite (0.33 g) was added to the mixture, which was quickly stirred for 10 min (and all of the color disappeared). Water (100 mL) was added and the mixture was quickly stirred for 10 min. The mixture was allowed to settle into layers, and the organic layer was pumped down to dryness. The residue was dissolved in chloroform (10 mL) and then it was diluted with ethyl acetate (~50 mL) to form insoluble materials. More chloroform was added until all of the solids dissolved. The solution was cooed to −50° C. for 30 min to form solids. After filtering it, the solids were washed with ethyl acetate/heptane (1:2, 2×5 mL). The solid was dried in vacuum to give 3.6 g of the product as off-white solids. The molar yield of the desired product was 78-86% in reaction solution and 65-75% after isolation. The product purity was 90-95% (area %).

Example 3

Synthesis of (+)-1-Bromocodeinone (+)-1-Bromocodeinone was prepared from (+)-1,7-dibromohydrocodone according to the following scheme:

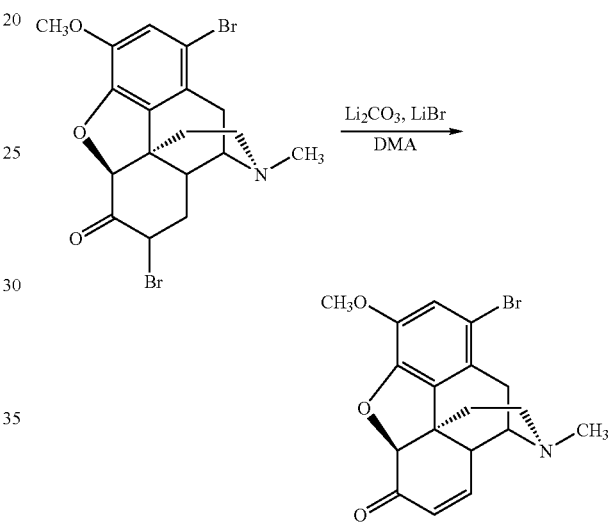

Trial 1. A flask containing a mixture of 1,7-dibromohydrocodone (0.15 g, 0.28 mmol, 1 eqv), LiBr (48 mg, 0.56 mmol, 2 eqv), $Li_2CO_3$ (114 mg, 1.53 mmol, 5.5 eqv) in 5 mL of dry DMF was heated under nitrogen to 120° C. for two hrs. The desired product (~8% integration area) was identified with HPLC and LC-MS analysis (MW+1=376.1).

Trial 2. A flask containing a mixture of 1,7-dibromohydrocodone (0.15 g, 0.28 mmol, 1 eqv), LiI (75 mg, 0.56 mmol, 2 eqv), $Cs_2CO_3$ (0.5 g, 1.53 mmol, 5.5 eqv) in 5 mL of dry DMF was heated under nitrogen to 90° C. for 30 min. The desired product (~8% integration area) was identified with HPLC and LC-MS analysis (MW+1=376.1).

Trial 3. A flask containing a mixture of 1,7-dibromohydrocodone (100 mg, 0.19 mmol, 1 eqv), LiBr (90 mg, 1.03 mmol, 5.4 eqv), $Li_2CO_3$ (114 mg, 1.53 mmol, 8 eqv) in 5 mL of dry N,N-dimethylacetamide was heated under nitrogen to 120° C. for 1.5 hr. The desired product (~32% integration area) was identified with HPLC and LC-MS analysis (MW+1=376.2).

Trial 4. A flask containing a mixture of 1,7-dibromohydrocodone (100 mg, 0.19 mmol, 1 eqv), LiBr (90 mg, 1.03 mmol, 5.4 eqv), $Li_2CO_3$ (114 mg, 1.53 mmol, 8 eqv) in 5 mL of dry N,N-dimethylacetamide was heated under nitrogen to 130° C. for 45 minutes. The desired product (20% integration area) was identified with HPLC.

Trial 5. A flask containing a mixture of 1,7-dibromohydrocodone (100 mg, 0.19 mmol, 1 eqv), LiBr (90 mg, 1.03 mmol, 5.4 eqv), $Li_2CO_3$ (114 mg, 1.53 mmol, 8 eqv) in 5 mL of dry N,N-dimethylacetamide was placed into a pre-heated oil bath at 120° C. for one hr. The desired product (~40% integration area) was identified with HPLC.

Example 4

Alternate Synthesis of (+)-1-Bromocodeinone

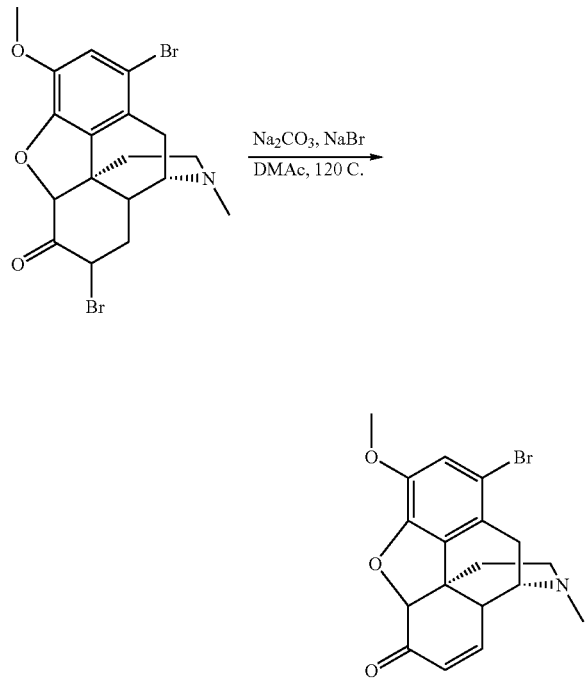

Li$_2$CO$_3$ (0.115 g, 1.56 mmol) and LiBr (0.090 g, 1.04 mmol) were added to 7 mL N,N-dimethyl acetamide at room temperature. The slurry was heated to 120° C. A room temperature solution of (+)-1,7-dibromohydrocodone in 3 mL N,N-dimethyl acetamide was added. The resulting slurry was heated at 120° C. for one hour. Analysis of the reaction by liquid chromatography showed 25.6 area % of (+)-1-bromocodeinone.

Example 5

Synthesis of (+)-Acylthebaine

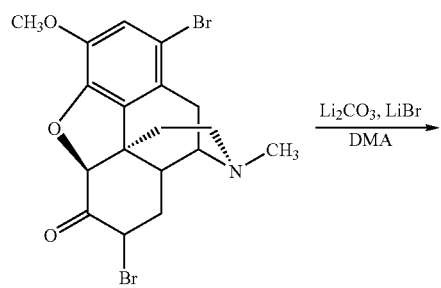

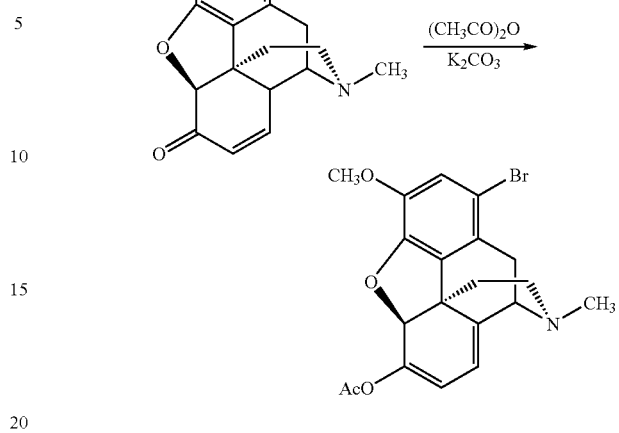

Trial 1. A flask containing a mixture of 1,7-dibromohydrocodone (100 mg, 0.19 mmol, 1 eqv), LiBr (90 mg, 1.03 mmol, 5.4 eqv), Li$_2$CO$_3$ (114 mg, 1.53 mmol, 8 eqv) in 5 mL of dry N,N-dimethylacetamide was heated under nitrogen to 120° C. for 1.5 hr. Then the reaction was cooled in ice bath for 10 min, to the reaction was added 200 mg powdered potassium carbonate and 300 μL of acetic anhydride. The reaction was then gradually heated to 110° C. for one hr. After cooling to room temperature, to the reaction was added 50 mL dichloromethane, the resulting mixture was washed with water (3×25 mL). The volatiles were removed by vacuum distillation to give a brown residue that contained about 40% desired product based on HPLC analysis.

Trial 2. A flask containing a mixture of 1,7-dibromohydrocodone (2.0 g, 3.8 mmol, 1 eqv), LiBr (1.8 g, 21 mmol, 5.4 eqv), Li$_2$CO$_3$ (2.3 g, 31 mmol, 8 eqv) in 100 mL of dry N,N-dimethylacetamide was placed in a pre-heated oil bath at 120-125° C. for 2 hr. Then the reaction was cooled in ice bath for 10 min, and 4 grams of powdered potassium carbonate and 6 mL of acetic anhydride were added to the reaction mixture. The reaction was then gradually heated to 110° C. for one hr. After cooling to room temperature, to the reaction was added 300 mL dichloromethane. The resulting mixture was washed with water (3×100 mL). The volatiles were removed on vacuum distillation to give a brown residue which contained about 50% desired product based HPLC analysis; LC-MS: MW+1=418.3.

Trial 3. A flask containing a mixture of 1,7-dibromohydrocodone (5.0 g, 9.3 mmol, 1 eqv), LiBr (4.5 g, 52.5 mmol, 5.6 eqv), Li$_2$CO$_3$ (5.75 g, 77.7 mmol, 8.4 eqv) in 250 mL of dry N,N-dimethylacetamide was placed in a pre-heated oil bath at 120-125° C. for 2 hr. Then the reaction was cooled in ice bath for 10 min, and 4 grams of powdered potassium carbonate and 6 mL of acetic anhydride were added to the reaction. The reaction was then gradually heated to 110° C. for one hr. After cooling to room temperature, 500 mL dichloromethane was added to the reaction. The resulting mixture was washed with water (3×200 mL). The volatiles were removed on vacuum distillation to give a brown residue, which contained about 40% desired product based on HPLC analysis. LC-MS: MW+1=418.3.

Example 6

Synthesis of (+)-Oxycodone

Trial 1. (+)-Acylthebaine (40 mg) was dissolved in acetic acid (0.5 mL) and water (0.5 mL) at room temperature (rt).

The reaction flask was flushed with nitrogen. Per-acetic acid (44 µL) was added. The reaction was stirred at rt for 60 min to form a mixture of (+)-14-hydroxycodeinone and (+)-14-hydroxycodeinone-OAc. The mixture was then treated with 5% Pd/C (2 mg) at rt for 30 min with stirring. More 5% Pd/C (2 mg) was added. The mixture was stirred under hydrogen (60 psi) at 60° C. for 3 h. Hydrogen was replaced by nitrogen and the reaction mixture was filtered. The solid was washed with water (2×2 mL). The solution mainly contained (+)-oxycodone (with little (+)-oxycodone-OAc).

Trial 2. Acylthebaine (40 mg) was dissolved in acetic acid (1.0 mL) at rt. The reaction mix was flushed with nitrogen. Per-acetic acid (44 µL) was added. The mixture was stirred at rt for 60 min to form a mixture of product that mainly contain (+)-14-hydroxycodeinone-OAc. The mixture was then treated with 5% Pd/C (2 mg) at rt for 30 min with stirring. More 5% Pd/C (2 mg) was added. The mixture was stirred under hydrogen (60 psi) at 60° C. for 3 h. Hydrogen was replaced by nitrogen and the reaction mixture was filtered. The solid was washed with water (2×2 mL). The solution mainly contained (+)-oxycodone-OAc. (+)-oxycodone-OAc was converted to (+)-oxycodone by adding c-HCl (1 mL) to the solution. The solution was heated at 90° C. for 1 h to give a solution of (+)-oxycodone and the area % of the product was 60-80%.

Trial 3. A solution of about 0.23 mol of (+)-14-hydroxycodeinone was charged with Pd/C (5%, 1.8 g). The reactor was purged 4 times with nitrogen and then 4 times with hydrogen. The reaction was stirred at rt under hydrogen pressure (40 PSI) for 10 min. The reaction was heated to 50° C. under hydrogen pressure (40 PSI) for 6 h, and then cooled to rt. The reactor was purged with nitrogen 4 times and a sample was removed for HPLC analysis. The reaction mixture was heated to 50° C. and filtered. The solid was washed with water (73 mL). The filtrate was cooled to 30-40° C. and flashed with nitrogen. The combined aqueous layers were diluted with IPA (20% of the volume), and the pH of the solution was adjusted to 7~7.5 and stirred at 30-40° C. for 30 min to form precipitate. Charged more c-$NH_4OH$ until pH=10 and heat it at 30-40° C. for 30 min. Cool down to 0-5° C. for 2 h and filter it. Washed the solid obtained with water (3×23 mL). Charge the wet cake on 27) to a flask. Charge water (4×73 mL). Adjust the pH to 4.5-5.5 with HOAc or c-$NH_4OH$. Charged activated charcoal (3.6 g) and filter aid (3.6 g). Heated at 60° C. for 30 min. Filtered the mixture. Washed the cake with water (73 mL). Adjusted the pH with c-$NH_4OH$ until crystals appeared (pH=7-8) while maintaining at 60° C. Stir for 30 min. Adjusted the pH with c-$NH_4OH$ until pH=10.4-11.8. Cooled down to 0-5° C. for 1 h. Filtered the mixture. Washed the solid with water (3×36 mL). Dried the wet solid in vacuum at 65° C. for 18 h to give 60.2 g of (+)-oxycodone as a white solid, in 87% yield (assay 98.61% % wt/wt).

Example 7

Synthesis of (+)—N-EtOCO-Noroxycodone from (+)-Oxycodone (+)-Oxycodone (31.5 g) was dissolved in chloroform (63 mL). $NaHCO_3$ (67 g) was added. EtOCOCl (57.2 mL) was added. The mixture was heated to 50° C. for 1 h and then at 60° C. (with slight reflux) for 9 h. The mixture was cooled to rt. Water (300 mL) was added and stirred for 30 min. The aqueous layer was extracted with chloroform (60 mL). The combined organic layer was washed with water (2×300 mL, adjust pH to 2-3 with HCl) and then water (300 mL). It was pumped down to sticky material that was dissolved in ethyl acetate (50 mL) and re-pumped down to dryness twice. It gave the product, (+)—N-EtOCO-noroxycodone as an orange solid, 42.1 g.

Example 8

Synthesis of (+)-Noroxycodone (+)—N-EtOCO-noroxycodone (from Example 7) was dissolved in $EtCO_2H$ (47.3 mL) at 80° C. and transferred to a three neck flask (250 mL). Water (47.3 mL) and $MeSO_3H$ (47.3 mL) were added under nitrogen. It was heated to 105° C. for 12 h. It was cooled down to rt overnight to give crystals. About 31 mL of the solvent was removed by vacuum distillation at 60° C. It was cooled down to rt. IPA (94.6 mL) was charged. It was cooled down to 0-5° C. for 2 h and filtered. The solid obtained was washed with IPA (2×10 mL) to give the product in 60% yield.

Example 9

Purification of (+)-Norhydrocodone to form (+)-Norhydrocodone.HBr (+)-Norhydrocodone (4.0 g, crude) was added to water (20 mL). It was heated at 60-70° C. for 0.5 h. 46% HBr was added until pH 4-5. It was heated for 0.5 h to give a solution. It was cooled down to 30-40 C. 5 mL of 46% HBr was added. It was stirred at 30-40° C. for 0.5 h and cooled to rt for 1 h. It was filtered. The wet solid was dried in vacuum at 60° C. for 18 h to give 2.85 g of solid.

Example 10

Conversion of (+)-Norhydrocodone to (+)-Norhydromorphone (+)-Norhydrocodone (4.0 g, crude) was dissolved in 46% HBr (20 mL). It was heated at 95° C. for 4 h. It was cooled down to rt and was diluted with water (30 mL) and treated with c-$NH_4OH$ until pH=8. It was extracted with chloroform (30 mL). The organic layer was pumped down to dryness to give solid. It contained (+)-norhydydromorphone.

Example 11

Conversion of (+)-Norhydrocodone.HBr to (+)-Norhydromorphone

Norhydrocodone (1.0 g) was suspended in dichloromethane/chlorobenzene (15 mL/15 mL). It was cooled to 0° C. $BBr_3$ (1.5 mL) was added. It was stirred at 0° C. for 1 h. It was allowed to warm up to rt and 4 N NaOH was added until pH=14. It was stirred for 15 min and settle into two layers. The aqueous layer was separated and the pH was adjusted to 8-10 with HOAc to form a solid. It was filtered. The solid was washed with water (2×1 mL). It was confirmed to be the product of (+)-norhydromorphone.

Example 12

Synthesis of (+)-Naltrexone from (+)-Oxymorphone

To a flask, the following materials were added: (+)-noroxymorphone (1.0 g), DMF (5.2 g), $NaHCO_3$ (0.64 g) and cyclopropyl bromide (0.611 g). The reaction mixture was flashed with nitrogen and heated to 85° C. (81-90° C.) for 3 h. It was cooled down to rt. Sample was checked with HPLC for the completion of the reaction [(+)-noroxymorphone to (+)-naltrexone was <50:1]. It was cooled down to room temperature and then water (14.9 g) was added while maintaining the reaction temperature <40° C. It was stirred at rt for 30 min and cooled to 0-5° C. for 3 h. It was filtered. The solid was washed with cooled water (0-5° C., 2×0.5 mL. The wet cake was 1.8 g and the product (+)-naltrexone was >90% pure (area/area, by HPLC analysis).

Example 13

Purification of (+)-Naltrexone (+)-Naltrexone (from Example 12) was dissolved in dichloromethane (30 mL). It was extracted with 0.5 N NaOH (2×10 mL). The aqueous layer was washed with dichloromethane (10 mL). The pH of the aqueous layer was adjusted to 10 to form solids. It was filtered. The solid was washed with water (2×2 mL). The solid was dried in vacuum at 65° C. for 18 h to give 0.6 g of solid, (+)-naltrexone, >97% pure.

What is claimed is:

1. A process for preparing compound 2-1, the process comprising contacting compound 2-1 (a) with a halogen, X, to form compound 2-1(b), and contacting compound 2-1(b) with a proton acceptor to form compound 2-1 according to the reaction scheme:

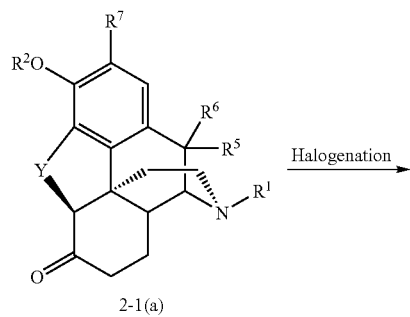
2-1(a)

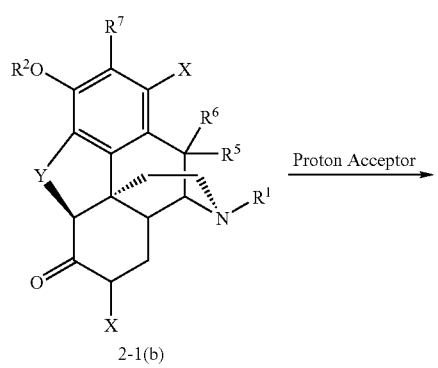
2-1(b)

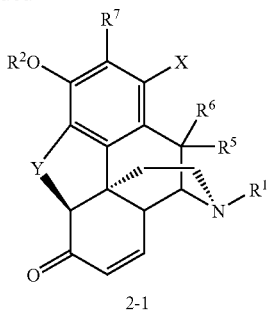
2-1 wherein:

R$^1$ and R$^2$ are independently selected from the group consisting of hydrogen, hydrocarbyl, substituted hydrocarbyl, and a protecting group;

R$^5$, and R$^6$ are independently selected from the group consisting of hydrogen, halogen, hydroxyl, NH$_2$, CN, hydrocarbyl, and substituted hydrocarbyl;

R$^7$ is selected from the group consisting of hydrogen and hydroxyl; and

Y is selected from the group consisting of oxygen, sulfur, and nitrogen.

2. The process of claim 1, wherein:

R$^1$ and R$^2$ are independently selected from the group consisting of hydrogen, alkyl, vinyl, aryl, {—}CH$_2$-aryl, acyl, alkoxycarbonyl, trialkylsily, oxygen protecting group, and a nitrogen protecting group;

R$^5$, R$^6$, and R$^7$ are each hydrogen;

Y is oxygen; and wherein the halogenation reaction is conducted in the presence of an organic solvent, the molar ratio of compound 2-1 (a) to halogen is from about 1:2 to about 1:10, and the halogenation reaction is conducted at a temperature ranging from about −40° C. to about 20° C.; the molar ratio of compound 2-1 (b) to proton acceptor is from about 1:1 to about 1:10 and the reaction is conducted at a temperature ranging from about 80° C. to about 140° C. in the presence of an aprotic solvent; and the configuration of carbons 5, 13, 14, and 9, respectively, of compounds comprising formulas 2-1(a), 2-1(b) and 2-1 is selected from the group consisting RRRS, RRSS, SRRS, SRSS, RSRR, RSSR, SSRR, and SSSR.

3. A process for the preparation of compound 8-1 according to the following reaction scheme:

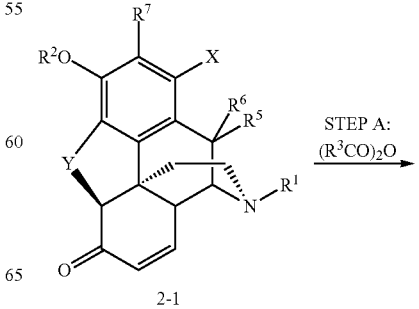
2-1

STEP A: (R$^3$CO)$_2$O

-continued

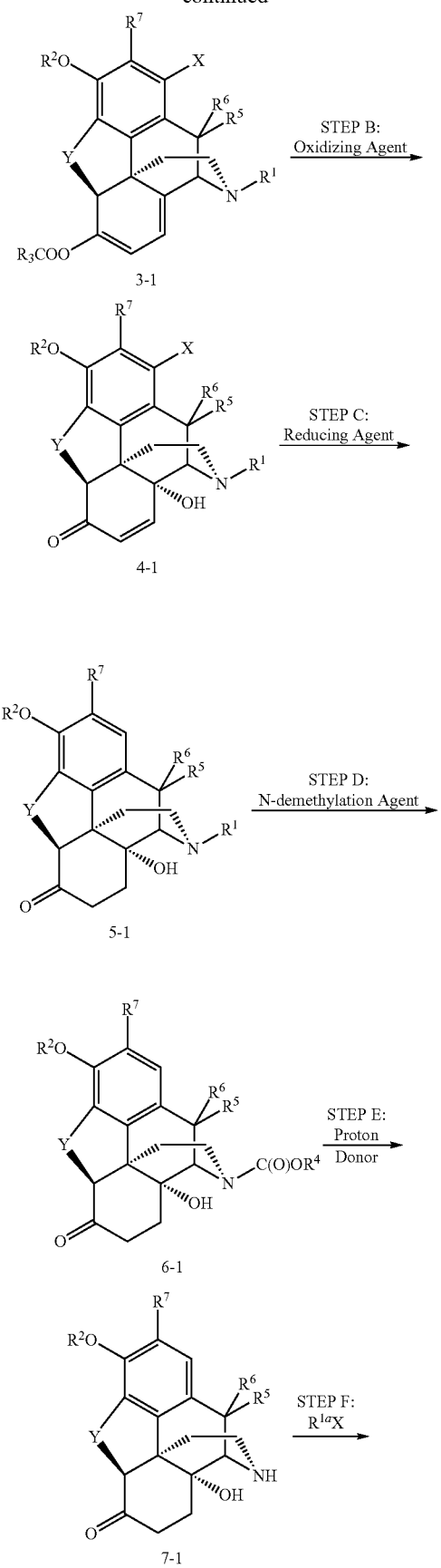

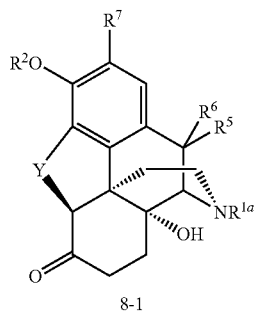

wherein:
R¹ and R² are independently selected from the group consisting of hydrogen and methyl;
$R^{1a}$ is selected from the group consisting of hydrocarbyl, and substituted hydrocarbyl;
R³ is selected from the group consisting of alkyl, substituted alkyl, aryl, and substituted aryl;
R⁴ is selected from the group consisting of hydrocarbyl, and substituted hydrocarbyl;
R⁵, and R⁶ are independently selected from the group consisting of hydrogen, halogen, hydroxyl, NH₂, SH, hydrocarbyl, and substituted hydrocarbyl, wherein R⁵, and R⁶ may together form a group selected from the group consisting of =O, and =S;
R⁷ is selected from the group consisting of hydrogen, halogen, hydroxyl, NH₂, CN, hydrocarbyl, and substituted hydrocarbyl;
X is selected from the group consisting of halogen and hydrogen; and
Y is selected from the group consisting of oxygen, sulfur, and nitrogen, and
wherein compound 2-1 is prepared by a process comprising contacting compound 1-1 with an alcohol scavenger in the presence of a proton donor to form compound 2-1 according to the following reaction scheme:

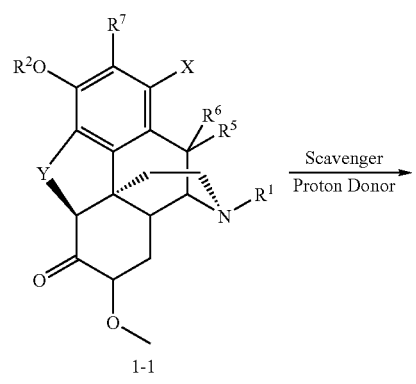

-continued

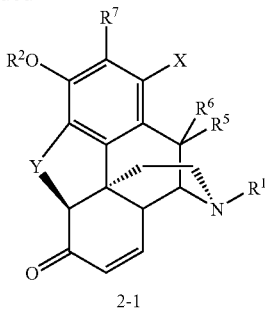

2-1 wherein R¹, R², R⁵, R⁶, R⁷, X, and Y are as defined above, the molar ratio of compound 1-1 to alcohol scavenger to proton donor is from about 1:0.5:2 to about 1:2:20, and the reaction is conducted in the presence of an aprotic solvent at a temperature ranging from about 20° C. to about 100° C., or wherein compound 2-1 is prepared by a process comprising contacting compound 2-1(a) with a halogen, X, to form compound 2-1(b), and contacting compound 2-1(b) with a proton acceptor to form compound 2-1 according to the reaction scheme:

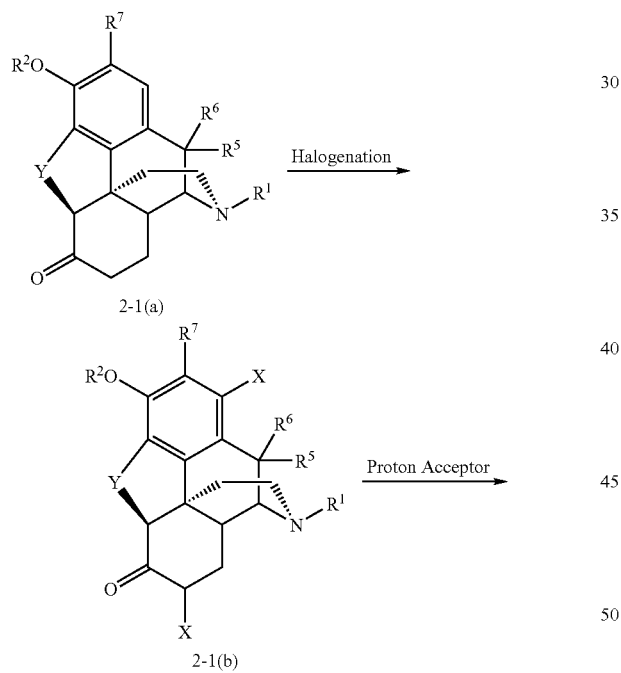

wherein R¹, R², R⁵, R⁶, R⁷ and Y are as defined above; the halogenation reaction is conducted in the presence of an organic solvent, the molar ratio of compound 2-1(a) to halogen is from about 1:2 to about 1:10, and the halogenation reaction is conducted at a temperature ranging from about −40° C. to about 20° C.; and the molar ratio of compound 2-1(b) to proton acceptor is from about 1:1 to about 1:10 and the reaction is conducted at a temperature ranging from about 80° C. to about 140° C. in the presence of an aprotic solvent.

4. The process of claim 3, wherein:

$R^{1a}$ is selected from the group consisting of alkyl, vinyl, aryl, {—}(CH₂-aryl;

$R^4$ is selected from the group consisting of alkyl, vinyl, aryl, {—}(CH₂-aryl;

X is bromide; and

Y is oxygen.

5. The process of claim 3, wherein $R^{1a}$ is {—}(CH₂-cyclopropyl, $R^2$ is hydrogen, and Y is oxygen.

6. The process of claim 3, wherein $R^{1a}$ is {—}(CH₂—CHCH₂, $R^2$ is hydrogen, and Y is oxygen.

7. The process of claim 3, further comprising a process for preparing compound 1-1, the process comprising contacting a compound comprising SM-1 with bromide to form a compound comprising SM-2, and contacting the compound SM-2 with sodium hydroxide to form the compound comprising 1-1 according to the following reaction scheme:

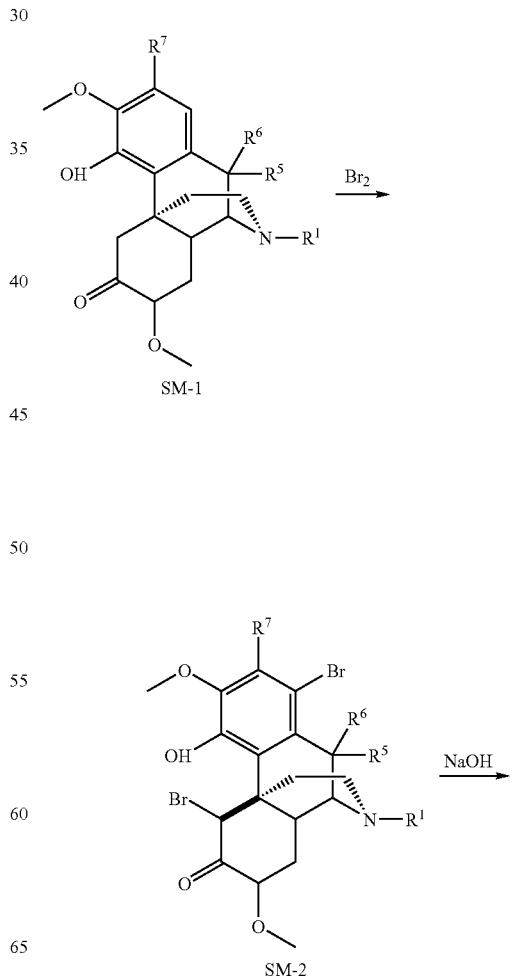

-continued

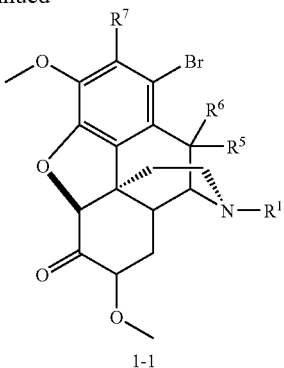

1-1 wherein: $R^1$, $R^5$, $R^6$, and $R^7$ are as defined in claim 3.

8. The process of claim 3, wherein the molar ratio of compound 2-1 to $(R^3CO)_2O$ is from about 1:2 to about 1:20, the reaction of Step A is conducted in the presence of an aprotic solvent and at a temperature ranging from about 20° C. to about 100° C.; the molar ratio of compound 3-1 to oxidizing agent is from about 1:1 to about 1:2, the reaction of Step B is conducted in the presence of a protic solvent; at a temperature ranging from about 0° C. to about 100° C.; the molar ratio of compound 4-1 to reducing agent is from about 1:0.0005 to about 1:0.005, the reaction of Step C is conducted in the presence of an aprotic solvent, and at a temperature ranging from about 20° C. to about 120° C.; the molar ratio of compound 5-1 to N-demethylation agent to proton acceptor is from about 1:2:1 to about 1:20:20, the reaction of Step D is conducted in the presence of an aprotic solvent, and at a temperature ranging from about 50° C. to about 120° C.; the molar ratio of compound 6-1 to proton donor is from about 1:2 to about 1:20, the reaction of Step E is conducted in the presence of a protic solvent, and at a temperature ranging from about 80° C. to about 120° C.; the molar ratio of compound 7-1 to $R^{1a}X$ is from about 1:1 to about 1:2, the reaction of Step F is conducted in the presence of an organic solvent, and at a temperature ranging from about 20° C. to about 120° C.

9. The process of claim 3, wherein the yield of compound 8-1 is from about 5% to about 45%.

10. The process of claim 3, wherein the configuration of carbons 5, 13, 14, and 9, respectively, of compounds comprising formulas 1-1 and 8-1 is selected from the group consisting RRRS, RRSS, SRRS, SRSS, RSRR, RSSR, SSRR, and SSSR.

* * * * *